United States Patent
Takahashi

(10) Patent No.: US 10,890,531 B2
(45) Date of Patent: *Jan. 12, 2021

(54) APPARATUS AND METHOD FOR FLUORESCENCE GRADING OF GEMSTONES

(71) Applicant: GEMOLOGICAL INSTITUTE OF AMERICA INC. (GIA), Carlsbad, CA (US)

(72) Inventor: Hiroshi Takahashi, Fort Lee, NJ (US)

(73) Assignee: Gemological Institute of America, Inc. (GIA), Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/666,375

(22) Filed: Oct. 28, 2019

(65) Prior Publication Data

US 2020/0064267 A1 Feb. 27, 2020

Related U.S. Application Data

(63) Continuation of application No. 16/133,454, filed on Sep. 17, 2018, now Pat. No. 10,488,341, which is a continuation of application No. 14/673,780, filed on Mar. 30, 2015, now Pat. No. 10,107,757.

(51) Int. Cl.
| | |
|---|---|
| *G01N 21/00* | (2006.01) |
| *G01N 21/64* | (2006.01) |
| *G01N 33/38* | (2006.01) |
| *G01N 21/87* | (2006.01) |

(52) U.S. Cl.
CPC ......... *G01N 21/6456* (2013.01); *G01N 21/87* (2013.01); *G01N 33/381* (2013.01); *G01N 2021/6471* (2013.01); *G01N 2201/062* (2013.01); *G01N 2201/068* (2013.01); *G01N 2201/0634* (2013.01); *G01N 2201/12* (2013.01)

(58) Field of Classification Search
None
See application file for complete search history.

(56) References Cited

U.S. PATENT DOCUMENTS

| | | |
|---|---|---|
| 5,118,181 A | 6/1992 | Yifrach et al. |
| 5,615,005 A | 3/1997 | Valente et al. |
| 5,835,205 A | 11/1998 | Hunter et al. |
| 6,239,867 B1 | 5/2001 | Aggarwal |

(Continued)

FOREIGN PATENT DOCUMENTS

| | | |
|---|---|---|
| CA | 2890047 A1 | 5/2014 |
| GB | 2293236 A | 3/1996 |

(Continued)

*Primary Examiner* — David P Porta
*Assistant Examiner* — Mamadou Faye
(74) *Attorney, Agent, or Firm* — DLA Piper LLP (US)

(57) ABSTRACT

Provided herein is an apparatus for assessing a fluorescence characteristic of a gemstone. The apparatus comprises an optically opaque platform for supporting a gemstone to be assessed, one or more light source to provide uniform UV and non-UV illumination, an image capturing component, and a telecentric lens positioned to provide fluorescent images of the illuminated gemstone to the image capturing component. Also provided are methods of fluorescence analysis based on images collected using such an apparatus.

20 Claims, 20 Drawing Sheets

(56) References Cited

U.S. PATENT DOCUMENTS

| | | |
|---|---|---|
| 6,473,164 B1 | 10/2002 | De Jong et al. |
| 6,509,559 B1 | 1/2003 | Ulrich et al. |
| 6,980,283 B1 | 12/2005 | Aggarwal |
| 7,102,742 B2 | 9/2006 | Geurts |
| 8,658,134 B2 * | 2/2014 | Chirila ............... G01N 33/6896 424/9.1 |
| 10,107,757 B2 | 10/2018 | Takahashi |
| 10,488,341 B2 * | 11/2019 | Takahashi ............ G01N 33/381 |
| 2004/0072137 A1 | 4/2004 | Lapa et al. |
| 2007/0285650 A1 | 12/2007 | Kemer et al. |
| 2009/0116082 A1 * | 5/2009 | Osa ...................... H04N 1/6052 358/501 |
| 2011/0212717 A1 | 9/2011 | Rhoads et al. |
| 2011/0228063 A1 | 9/2011 | Smith et al. |
| 2011/0310246 A1 | 12/2011 | Hornabrook et al. |
| 2012/0007971 A1 * | 1/2012 | Schnitzer ............. G01N 33/381 348/61 |
| 2013/0208085 A1 | 8/2013 | Marion et al. |
| 2014/0098370 A1 | 4/2014 | Ahner et al. |
| 2015/0346108 A1 | 12/2015 | Palmieri et al. |
| 2017/0343493 A1 * | 11/2017 | Reischig ................ G01N 23/20 |

FOREIGN PATENT DOCUMENTS

| | | |
|---|---|---|
| JP | H07239303 A | 9/1995 |
| JP | H07333158 A | 12/1995 |
| JP | 2003507735 A | 2/2003 |
| JP | 2010334725 A | 2/2013 |
| JP | 2013518274 A | 5/2013 |
| RU | 2009134802 A | 3/2011 |
| TW | 433463 U | 5/2001 |
| WO | WO9704302 A1 | 2/1997 |
| WO | WO0114854 A1 | 3/2001 |
| WO | WO2011092493 A2 | 8/2011 |

\* cited by examiner

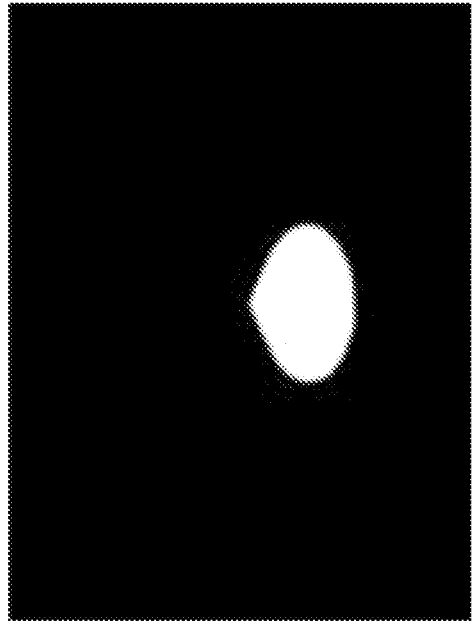
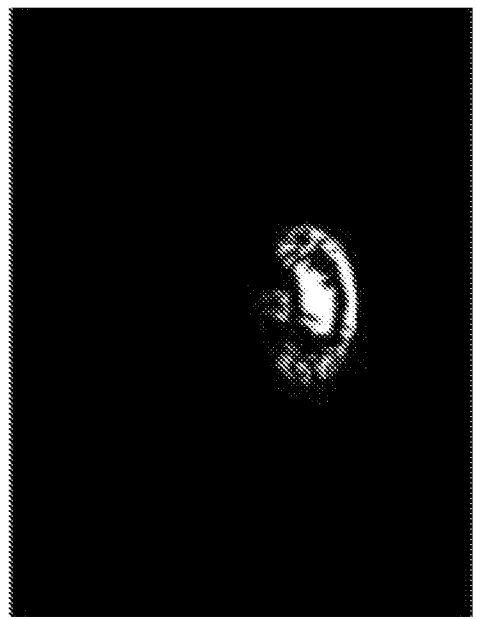
FIG. 7E
FIG. 7F

Reference stones

| None - Faint | Faint - Medium | Medium - Strong | Strong – Very strong |
|---|---|---|---|
| L: 18.8<br>C: 30.0<br>H: -77.7 | L: 33.2<br>C: 37.7<br>H: -78.6 | L: 59.6<br>C: 50.7<br>H: -84.9 | L: 79.8<br>C: 35.8<br>H: -121.5 |

FIG. 11

| Sample Number | Shape: weight | Visual Grade | Instrument Grade |
|---|---|---|---|
| 1 | Emerald: 1.32 ct | None | None |
| 2 | Oval: 1.15 ct | Faint | Faint |
| 3 | Cushion: 0.7 ct | Faint | Faint |
| 4 | Cushion: 1.75 ct | Strong | Strong |

FIG. 13

| Sample Number | Shape: weight | Visual Grade | Instrument Grade |
|---|---|---|---|
| 5 | Cushion: 0.8 ct | Medium Green | Medium Green |
| 6 | RBC: 0.52 ct | Faint Yellow | Faint Yellow |

FIG. 14

| Sample Number | Shape: weight | Visual Grade | Instrument Grade |
|---|---|---|---|
| 7 | Perl: 1.53 ct | Medium Yellow | Medium Yellow |
| 8 | RBC: 0.65 ct | Medium Orange | Medium Orange |

FIG. 15

APPARATUS AND METHOD FOR FLUORESCENCE GRADING OF GEMSTONES

CROSS-REFERENCE TO RELATED APPLICATIONS

This application is a continuation of and claims priority to U.S. patent application Ser. No. 16/133,454 filed Sep. 17, 2018 which in turn claims priority to U.S. patent application Ser. No. 14/673,780 filed Mar. 30, 2015 and entitled "Apparatus and Method for Fluorescence Grading of Gemstones," the content of which are incorporated herein by reference in its entirety.

FIELD

The apparatus and methods disclosed herein generally relate to fluorescence grading of gemstones, in particular cut gemstones. In particular, the apparatus and methods relate to fluorescence grading of cut gemstones of irregular or fancy shapes. The apparatus and methods disclosed herein further relate to digital image processing based on color component analysis.

BACKGROUND

Diamonds and other gemstones are often analyzed and graded by multiple trained and skilled individuals, based upon their visual appearance. For example, the foundation of diamond analysis comprises analysis of the Four C's (color, clarity, cut and carat weight), two of which, color and clarity, have been traditionally evaluated by human inspection. Gemstones are also assessed for unusual visual qualities. For example, certain gemstones produce fluorescence emission under UV illumination, the extent and distribution of such fluorescence are also used to grade such gemstones. Like color and clarity grading, fluorescence grading was previously primarily assessed based on human visual perception. Analysis and grading requires the exercise of judgment, the formation of opinions and the ability to draw fine distinctions based on visual comparisons.

A process of inspection and analysis is often time-consuming, involving multiple rounds of inspections, measurements and checks by each trained and experienced individual. The process also involves quality control and may include a variety of non-destructive tests to identify treatments, fillings or other defects that may affect the quality of a specimen. Finally, the process includes intensive visual comparison of the diamond with a reference set of diamond master stones that serve as a historical standard with respect to diamond color and fluorescence.

Instruments have been created to improve efficiency and to permit gemstone analysis in the absence of trained and experienced individuals. For example, U.S. Pat. No. 7,102,742 to Geurtz et al. discloses a gemstone fluorescence measuring device that includes an ultraviolet ("UV") emission chamber, a UV radiation source, and a light meter assembly. The UV radiation source includes an upper light emitting diode ("LED") and a lower LED that radiate a gemstone under test from both above and below the gemstone. However, current instrument cannot provide consistent and reproducible fluorescence grade to fancy shape cut stones; such gemstones that are classified as Step Cuts, Hearts, Marquises, Ovals, Pears, Triangles, Princess cut, or any other cuts rather than round brilliant cut (RBC). Additionally, current instrument cannot provide hue information and an operator must input the color of fluorescence manually. This leads to the incorrect grading since it is not easy to see the color of weak fluorescence by human eyes.

What is need are apparatus and methods that can provide gemstone assessment and grading (e.g., fluorescence grading) as consistent and accurate as assessment and grading provided by trained and experienced individuals.

SUMMARY

In one aspect, provided herein is an apparatus for assessing a fluorescence characteristic of a gemstone. The apparatus comprises an optically opaque platform, where the platform has a surface configured to support a gemstone to be assessed; a light source shaped to at least partially enclose the platform, where the light source is about the same level as or below the surface of platform and designed to provide uniform ultraviolet (UV) radiation to the gemstone on the platform; an image capturing component, where the image capturing component is positioned at a predetermined angle relative to the platform surface that supports the gemstone, and where the image capturing component and platform are configured to rotate relative to each other; and a telecentric lens positioned to provide an image of the illuminated gemstone to the image capturing component.

In one aspect, provided herein is an apparatus for assessing a color characteristic of a gemstone. The apparatus comprises an optically opaque platform, where the platform has a surface configured to support a gemstone to be assessed; a light source above the surface of the platform, where the light source is designed to provide uniform ultraviolet (UV) radiation to the gemstone on the platform; an image capturing component, where the image capturing component is positioned at a predetermined angle relative to the platform surface that supports the gemstone, and where the image capturing component and platform are configured to rotate relative to each other; and a telecentric lens positioned to provide an image of the illuminated gemstone to the image capturing component.

In some embodiments, the apparatus further comprises a collimation lens, where the collimation lens and the light source are coupled to provide uniform UV illumination to the gemstone on the platform.

In some embodiments, the apparatus further comprises an optical diffuser, wherein the optical diffuser and the light source are coupled to provide uniform UV illumination to the gemstone on the platform.

In some embodiments, the apparatus further comprises a collimation lens, and an optical diffuser, where the collimation lens, optical diffuser and the light source are coupled to provide uniform UV illumination to the gemstone on the platform.

In some embodiments, the apparatus further comprises a reflector device having an inner surface that is at least partially spherical and comprises a reflective material. The reflector device at least partially covers the light source and platform surface, and directs UV radiation from the light source towards the gemstone positioned on the platform surface. In some embodiments, the inner surface of the reflector device has a hemispherical shape.

In some embodiments, the apparatus further comprises a computer readable medium for storing the images collected by the image capturing component.

In some embodiments, the apparatus further comprises an interface between the light source and platform surface for adjusting the output intensity of the UV radiation.

In some embodiments, the apparatus further comprises a UV filter between the image capturing component and the telecentric lens to eliminate all UV components.

In some embodiments, the UV radiation provided by the light source comprises trans-radiation, direct-UV radiation, and a combination thereof.

In some embodiments, the light source further provides uniform non-UV illumination to the gemstone.

In some embodiments, the telecentric lens is an object-space telecentric lens or a double telecentric lens.

In some embodiments, the platform is configured to rotate around a rotational axis that is perpendicular to the side of the platform where the gemstone is positioned.

In some embodiments, the platform is configured to rotate 360 degrees around the rotational axis.

In some embodiments, the platform is a flat circular platform, and wherein the rotational axis is through the center of the circular platform.

In some embodiments, the platform surface comprises a UV reflective material.

In some embodiments, the platform surface comprises a diffuse UV reflective material.

In some embodiments, the platform surface comprises a white diffuse reflective material.

In some embodiments, the light source is configured as a ring light surrounding the platform surface. In some embodiments, the light source comprises a plurality of light emitting LEDs. In some embodiments, the LEDs emits fluorescence at 365 nm or 385 nm.

In some embodiments, the LEDs are coupled with a bandpass filter. In some embodiments, the bandpass filter is set at 365 nm or 385 nm.

In some embodiments, the LEDs are configured as a ring light surrounding the platform surface.

In some embodiments, the light source comprises a daylight approximating light source and a plurality of light emitting LEDs. In some embodiments, the LEDs are coupled with a bandpass filter. In some embodiments, the bandpass filter is set at 365 nm or 385 nm.

In some embodiments, the predetermined angle between the image capturing component and the platform surface is between approximately zero and approximately 45 degrees. In some embodiments, the predetermined angle between the image capturing component and the platform surface is between approximately 10 and approximately 35 degrees.

In some embodiments, the image capturing component is selected from the group consisting of a color camera, a CCD camera, and one or more CMOS sensors.

In some embodiments, the image capturing component a plurality of color images of the gemstone illuminated by UV radiation, each image comprising a full image of the gemstone.

In some embodiments, the image capturing component captures a plurality of color images of the illuminated gemstone, where each image is taken when the image capturing component and the platform surface are at a different relative rotational position, and wherein each image comprises a full image of the gemstone.

In some embodiments, the plurality of color images comprises 4 or more color images, 5 or more color images, 10 or more images, 15 or more images, 20 or more images, or 800 or more images, and wherein each image is taken at a unique image angle and comprises a plurality of pixels.

In some embodiments, the fluorescence characteristic is a fluorescence intensity level, a fluorescence color, or a combination thereof.

In one aspect, provided herein is a method of assessing a fluorescence characteristic of a sample gemstone. For example, the method comprises the steps of (i0 determining a fluorescence mask for a fluorescent image in a plurality of fluorescent images based on an outline mask determined from an image in a plurality of images and an apparent fluorescence area based on the fluorescent image, (ii) quantifying individual color components in each pixel in the fluorescence mask in the fluorescent image of the plurality of fluorescent images, thereby converting values for individual color components to one or more parameters representing the color characteristic of each pixel; (iii) determining an average value for each of the one or more parameters for all pixels in the defined area in all images of the plurality of fluorescent image; and (iv) calculating a first fluorescence score of a sample gemstone based on the average values of the one or more parameters of all pixels in the defined area in all images of the plurality of fluorescent images.

Here, each image of the plurality of images comprises a full image of the sample gemstone being illuminated by non-UV light source. Each image of the plurality of fluorescent images comprises a full image of the sample gemstone being illuminated by uniform UV light source. In addition, the image and the fluorescent image are captured under identical conditions except the illumination light source;

In some embodiments, the method further comprises a step of (v) calculating a second fluorescence score of a sample gemstone based on pixels in the outline masks for all images of the plurality of fluorescent images.

In some embodiments, the method further comprises a step of (vi) assessing the fluorescence characteristic of the sample gemstone by comparing the first or second fluorescence score to values of corresponding fluorescence scores of one or more control fluorescence gemstones which are previously determined.

In some embodiments, the first fluorescence score reflects the color of the fluorescence and wherein the second fluorescence score reflects the strength.

In some embodiments, the method further comprises a step of collecting the plurality of images of the sample gemstone using an image capturing component at uniquely different image rotational angles while maintaining a constant image view angle.

In some embodiments, the method further comprises a step of collecting the plurality of fluorescent images of the sample gemstone using an image capturing component at uniquely different image rotational angles while maintaining a constant image view angle. Here, each fluorescent image in the plurality of fluorescent images corresponds to an image in the plurality of image and both are captured under identical image rotational angle and image view angle.

In some embodiments, the method further comprises a step of determining a fluorescence mask for each fluorescent image in the plurality of fluorescent images.

In some embodiments, the method further comprises a step of quantifying individual color components in each pixel in the fluorescence mask in each fluorescent image of the plurality of fluorescent images.

In some embodiments, the method further comprises the steps of collecting a new plurality of fluorescent images of the sample gemstone using the image capturing component at the uniquely different image rotational angles while maintaining the constant image view angle, wherein there is a time gap between the time when the plurality of fluorescent images is collected and the time when the new plurality of fluorescent images is collected; assigning a new fluorescent grade based on the new plurality of fluorescent images by applying steps (i) through (vi); and comparing the fluorescent grade and the new fluorescent grade based on the time gap.

In some embodiments, the time gap is between 2 minutes and 5 hours.

One of skill in the art would understand that any embodiment described herein can be used, when applicable, in connection with any aspect of the apparatus or method.

BRIEF DESCRIPTION OF THE DRAWINGS

Those of skill in the art will understand that the drawings, described below, are for illustrative purposes only. The drawings are not intended to limit the scope of the present teachings in any way.

FIG. 7E depicts an exemplary embodiment, showing extraction of an outline mask.

FIG. 7F depicts an exemplary embodiment, showing extraction of an apparent fluorescence area.

FIG. 11 depicts an exemplary embodiment, illustrating different strengths in fluorescence emission.

FIG. 13 depicts an exemplary embodiment, illustrating fluorescence emission in gemstones of different shapes.

FIG. 14 depicts an exemplary embodiment, illustrating fluorescence emission in different colors.

FIG. 15 depicts an exemplary embodiment, illustrating fluorescence emission in different colors.

DETAILED DESCRIPTION

Figure 1:
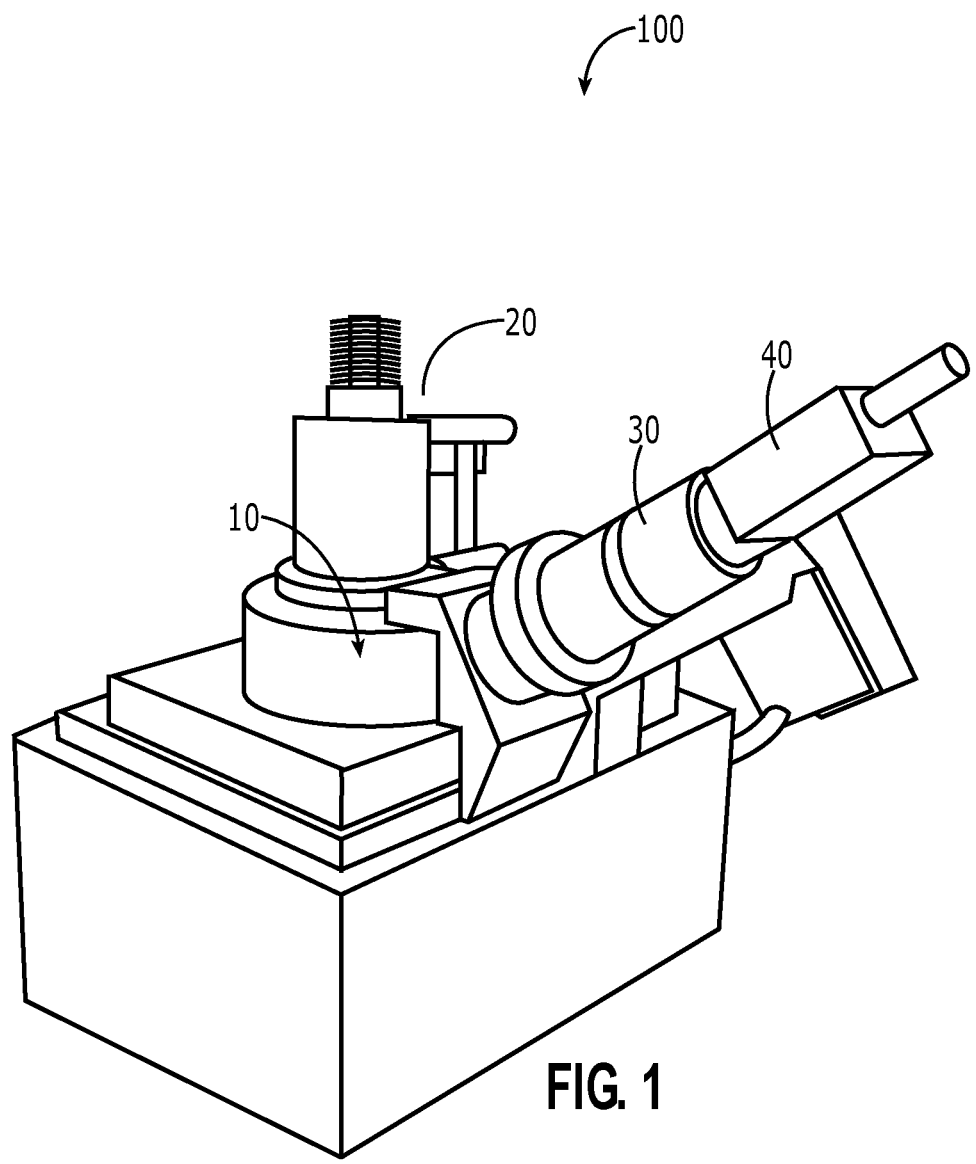
FIG. 1 depicts an exemplary embodiment of a gemstone optical assessment system including an optical unit and a gemstone evaluation unit.

Unless otherwise noted, terms are to be understood according to conventional usage by those of ordinary skill in the relevant art. For illustration purposes, diamonds are used as the representative gemstones. One of skill in the art would understand that the apparatuses, systems and methods disclosed herein are applicable to all types of gemstones capable of emitting fluorescence upon UV exposure. Systems and methods for color grading based on similar apparatuses are disclosed in U.S. patent application Ser. No. 14/673,776 (U.S. Pat. No. 9,678,081), entitled "APPARATUS AND METHOD FOR ASSESSING OPTICAL QUALITY OF GEMSTONES" and filed on Mar. 30, 2015 concurrently herewith, which is hereby incorporated by reference herein in its entirety.

As noted in the background, current automated instrument fails to provide accurate, complete and consistent assessment of the fluorescence property of certain gemstones (such as those of irregular or fancy shapes). One reason to account for the failure is that fluorescence intensity of a gemstone is affected significantly by a number of factors such as the orientation of the gemstone in relation to the detector, the position of gemstone, and the size of gemstone. In addition, some gemstones exhibit inhomogeneous distribution of fluorescence and current instrument cannot provide reproducible fluorescence grade for such stones, even if the gemstones are of regular round brilliant cut (RBC).

In order to overcome the existing issues, an improved fluorescence grading instrument as disclosed herein has the following characteristics: (1) to provide consistent and reproducible fluorescence grade to gemstones with no limitation from their sizes and shapes (2) to provide consistent and reproducible fluorescence color; (3) to provide consistent and reproducible fluorescence grade with easy and quick operation (e.g., operators do not need to put stones in the same position).

In one aspect, provided herein is an improved fluorescence grading apparatus for fluorescence assessment of gemstones such as cut diamonds. The apparatus is suitable for grading gemstones such as cut diamonds, including gemstones of irregular shapes, sizes, colors, and fluorescence distribution. An exemplary apparatus 100 is illustrated in FIG. 1, which includes but is not limited to, for example, a gemstone evaluation component 10, a light source with a UV filter 20, a telecentric lens 30, and an image capturing component 40.

Based on functionality, the components of an apparatus disclosed herein can be divided into two main units: a gemstone presentation unit and an optical unit. The gemstone presentation unit provides uniform illumination to gemstones being analyzed and the optical unit captures images of gemstones being presented.

Additionally and not depicted in FIG. 1, an exemplary apparatus further comprises a computer processing unit for analyzing information collected by the image capturing component.

Figure 2A:
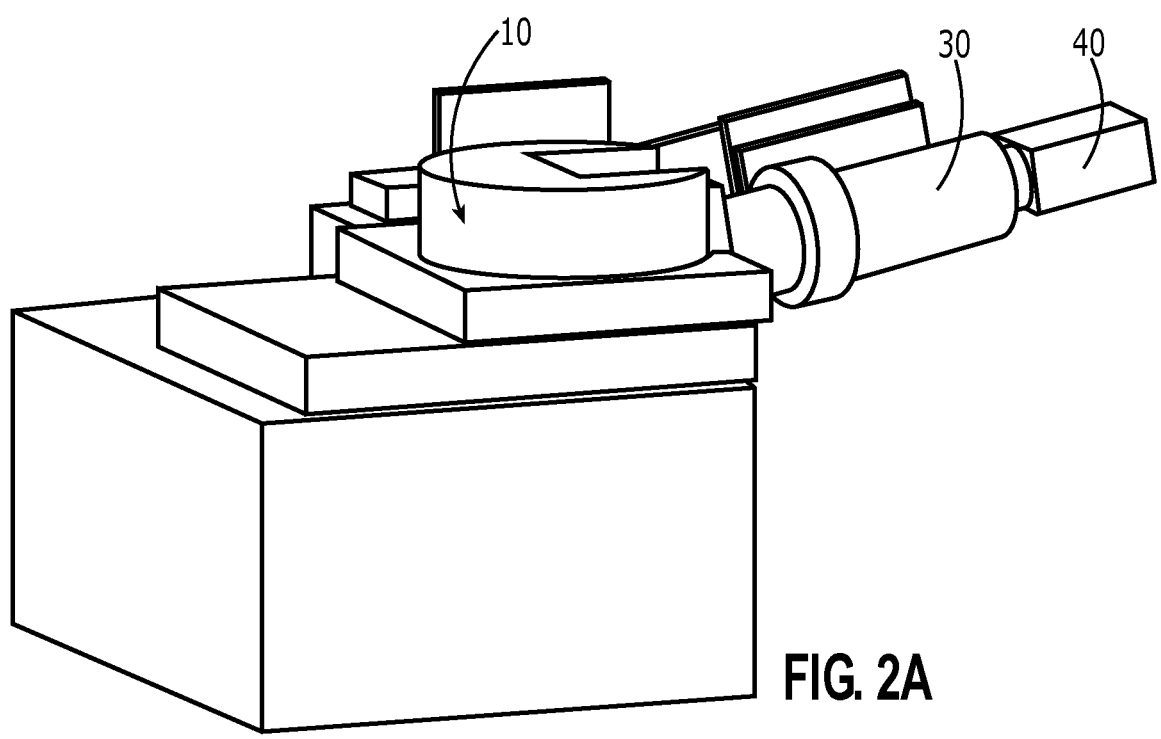
FIG. 2A depicts an exemplary schematic embodiment of a gemstone optical assessment system in a closed configuration (light source not shown).
Figure 2B:
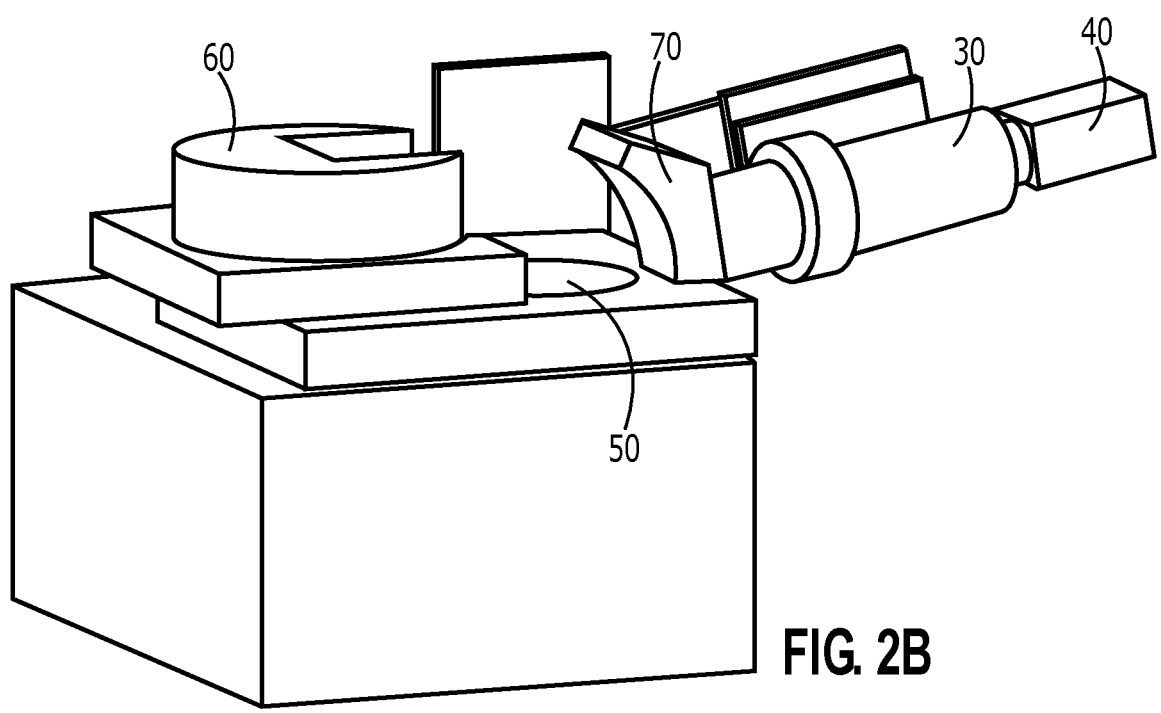
FIG. 2B depicts an exemplary schematic embodiment of a gemstone optical assessment system in an opened configuration (light source not shown).

As illustrated in FIG. 1, an exemplary gemstone presentation unit in turn comprises at least two parts: gemstone evaluation component 10 and a light source 20. The gemstone evaluation component is where a gemstone is presented. As depicted in FIGS. 2A and 2B, the gemstone evaluation component has a closed and an open configuration. Here, in order to clearly illustrate the different configurations, light source 20 is omitted in FIGS. 2A and 2B. In the closed configuration (see, e.g., FIG. 2A), a gemstone subject to analysis is completely concealed and not visible from an observer. In some embodiments, in order to avoid the inconsistencies caused by ambient light or other light, gemstone evaluation component is isolated and closed system from which ambient light or other light is excluded. The gemstone evaluation component and optic unit are joined in a complementary manner such that ambient light or other light is excluded from a concealed sample chamber within which a sample gemstone is housed. Although the fluorescence light source is not depicted in FIGS. 2A and 2B, one of skill in the art would understand that such as light source is required for fluorescence grading of gemstones.

Under the closed configuration, image information concerning the gemstone being analyzed is received and captured by the optical unit, which comprises a telecentric lens 30 and an image capturing device 40 (e.g., a camera).

In the open configuration (see, e.g., FIG. 2B), no image information is collected. Instead, the gemstone subject to analysis is exposed to an observer. In the open configuration, the gemstone presentation unit is revealed to have two parts: a bottom presentation component 50 and a top reflector component 60. In some embodiments, as illustrated in FIG. 2B, the top reflector component is mounted on movable side tracks. When the top reflector is moved on these tracks away from the optical unit, the bottom presentation component 50 is exposed. As shown in FIG. 2B, the shape and design of the opening of the top reflector component 60 is complementary to the shape and design of the optical connector module (e.g., element 70 in FIG. 2B) of the optical unit. In some embodiments, the optical connector module is a lens hood to which the telecentric lens 30 is attached.

Figure 3:
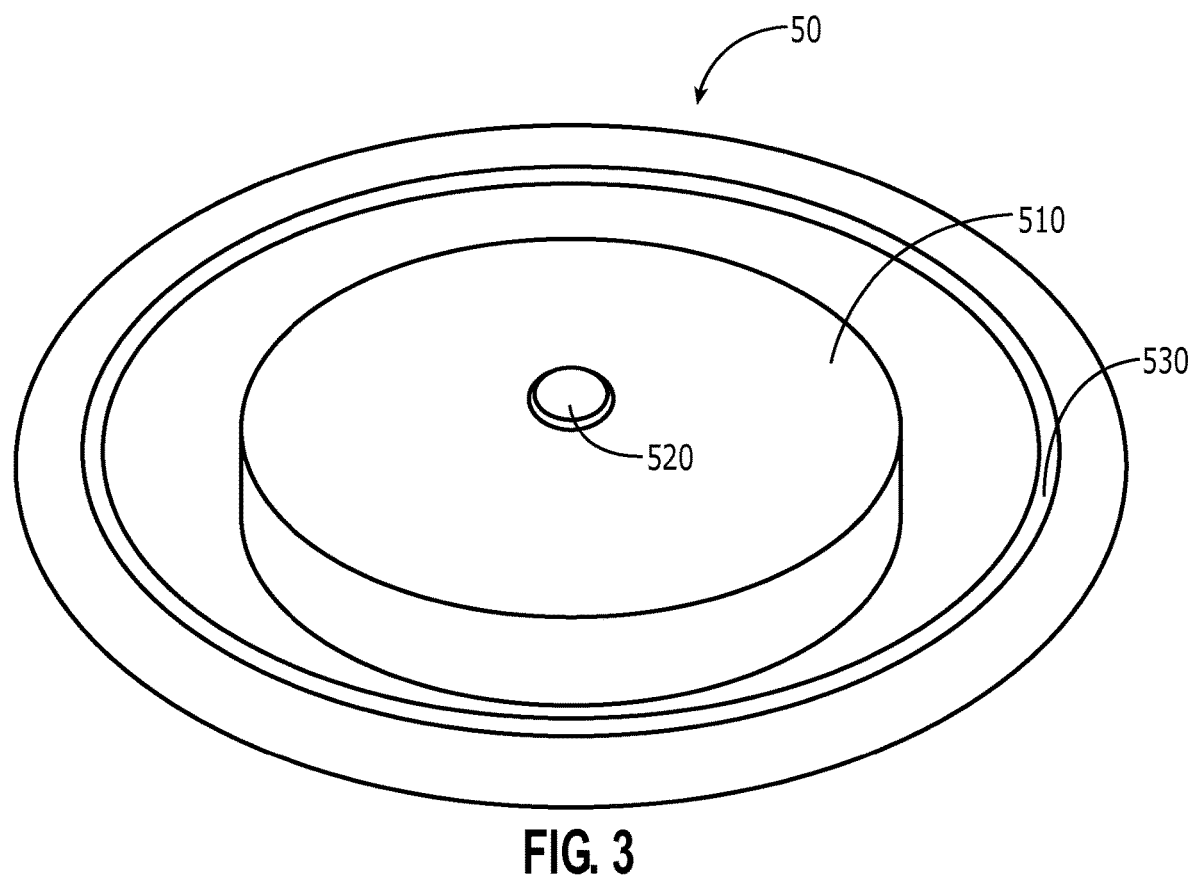
FIG. 3 depicts an exemplary embodiment of a sample platform with surrounding ring light illumination.

An exemplary bottom presentation component 50 is illustrated in FIG. 3. A circular white reflective platform 510 functions as the base on which a sample gemstone 520 is placed. A concentric circular ring light 530 is placed outside the circular platform such that the platform is completely enclosed within ring light 530.

Platform 510, also referred to as a stage or sample stage, is critical for the system disclosed herein. Importantly, it provides support to a gemstone that is being analyzed. In some embodiments, the top surface of the platform is a horizontal and flat. In addition, it functions as a stage for data collection by telecentric lens 30 and image capturing device 40 and subsequent analysis. In order to achieve data consistency, telecentric lens 30 is positioned at a first pre-determined angle relative to the top surface of platform 510. In some embodiments, image capturing device 40 is positioned at positioned at a second pre-determined angle relative to the top surface of platform 510. In some embodiments, the first and second pre-determined angles are the same and it has been optimized for data collection. In some embodiments, the first and second pre-determined angles are different, but each has been optimized for data collection. The first and second pre-determined angles can be referred to as the image or camera view angle.

Figure 4:
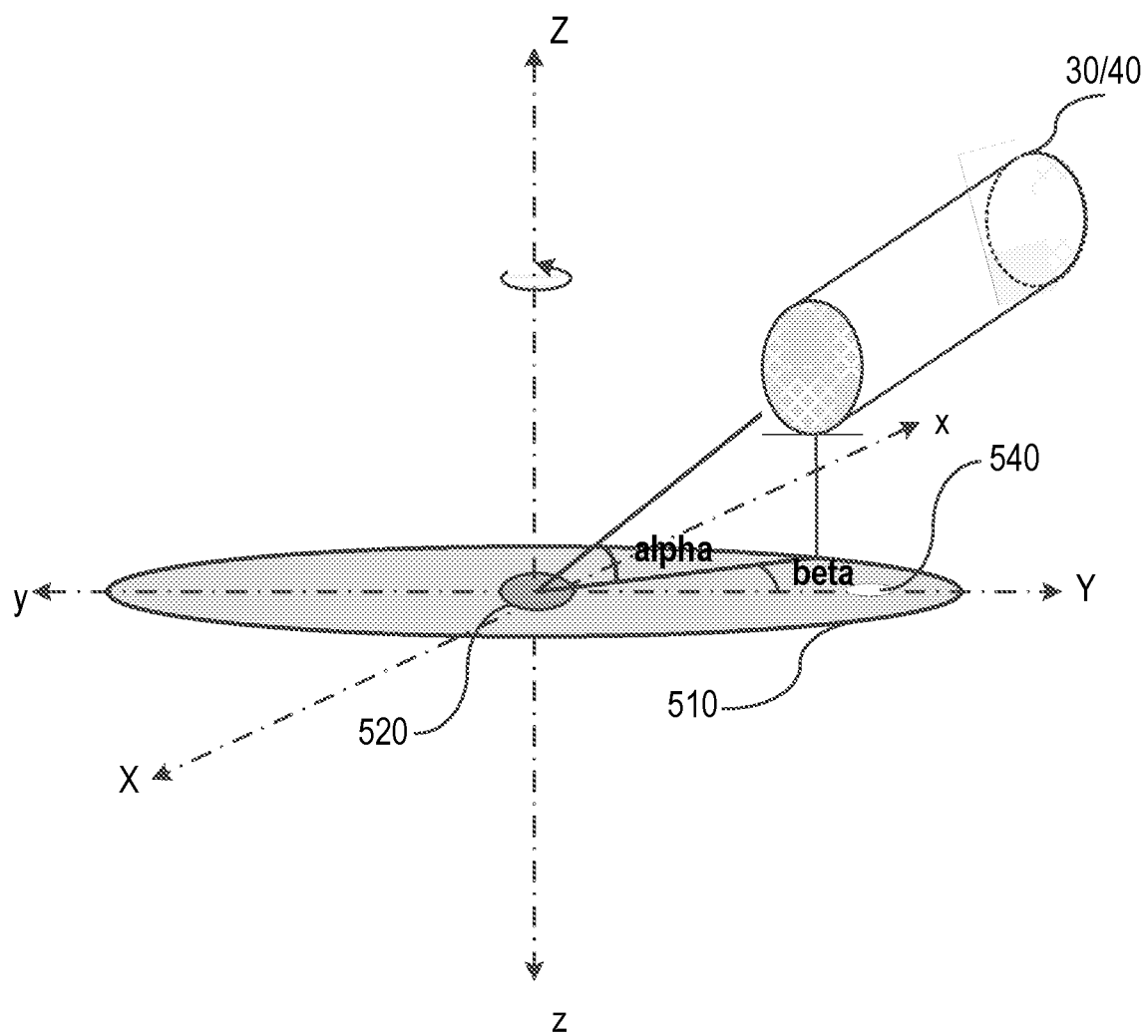
FIG. 4 depicts an exemplary schematic illustrating image view angle and image rotational angle.
Figure 5A:
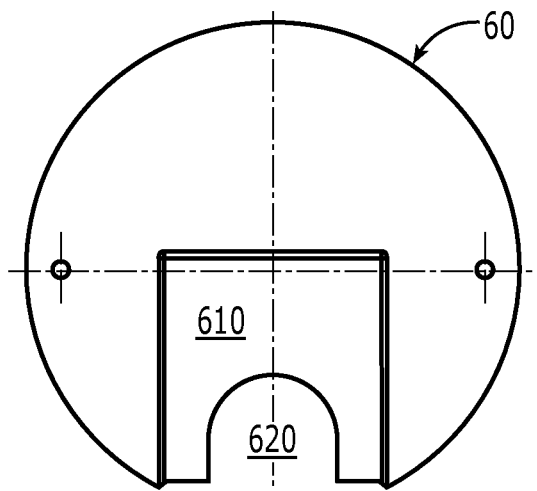
FIG. 5A depicts an exemplary embodiment of a top reflector with internal reflective surface.
Figure 5B:
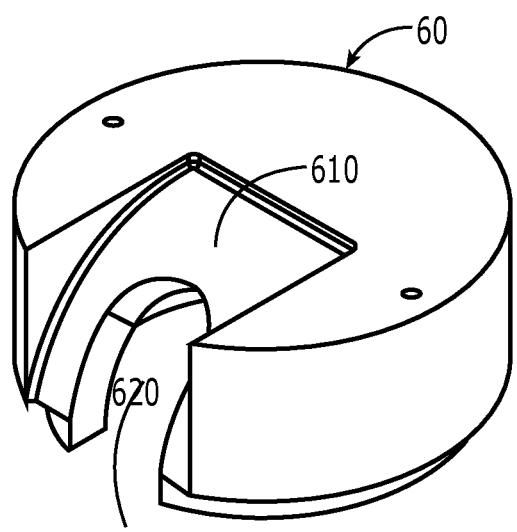
FIG. 5B depicts an exemplary embodiment of a top reflector with internal reflective surface.
Figure 5C:
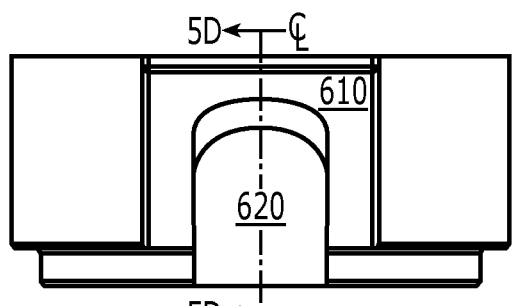
FIG. 5C depicts an exemplary embodiment of a top reflector with internal reflective surface.
Figure 5D:
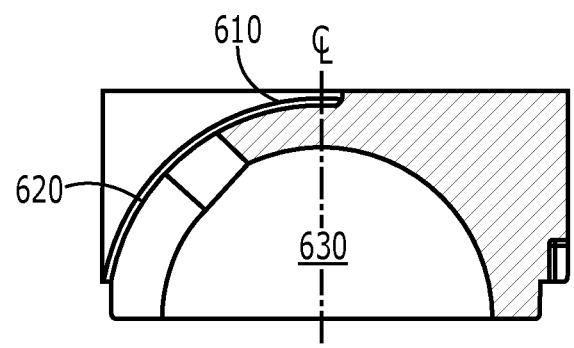
FIG. 5D depicts an exemplary embodiment of a top reflector with internal reflective surface.

An exemplary illustration of the relative configuration of the top surface of platform 510 to the optical unit (e.g., telecentric lens 30 and camera 40) is depicted in FIG. 4. Here, the optical unit, including both telecentric lens 30 and image capturing device 40, is positioned at a pre-determined angle (alpha) relative to the platform surface.

In some embodiments, the circular reflective platform is rotatable. For example, the platform is mounted on or connected with a rotor. In preferred embodiments, a gemstone being subjected to analysis is placed at the center of the platform surface, as illustrated in FIG. 3. The platform is then rotated in relation to the optical unit such that images of the gemstone at different angles are collected by the image capturing device.

In some embodiment, the platform surface is rotated around a rotational axis that goes through the center of origin of the circular platform surface and is perpendicular to the platform surface; see, for example, axis Zz depicted in FIG. 4.

In some embodiments, the platform is rotated in relation to the optical unit at set angular variations. The magnitude of the angular variations determines the extent of data collection; for example, how many images will be collection of the gemstone. For example, if the platform is rotated at an angular variation of 12 degree, a full rotation will allow 30 images of the gemstone to be collected. The angular variation can be set at any value to facilitate data collection and analysis. For example, the platform can be rotated at an angular variation of 0.5 degree or smaller, 1 degree or smaller, 1.5 degree or smaller, 2 degree or smaller, 3 degree or smaller, 4 degree or smaller, 5 degree or smaller, 6 degree or smaller, 7 degree or smaller, 8 degree or smaller, 9 degree or smaller, 10 degree or smaller, 12 degree or smaller, 15 degree or smaller, 18 degree or smaller, 20 degree or smaller, 24 degree or smaller, 30 degree or smaller, 45 degree or smaller, 60 degree or smaller, 90 degree or smaller, 120 degree or smaller, 150 degree or smaller, or 180 degree or smaller. It will be understood that the angular rotational variation can be set at any number. It will also be understood that the platform can be rotated for a total rotational angle of any value, not limited to a 360 degree full rotation. In some embodiments, data (e.g., color images) are collection for a rotation less than a 360 degree full rotation. In some embodiments, data (e.g., color images) are collection for a rotation more than a 360 degree full rotation.

In some embodiments, the platform or a portion thereof (e.g., the top surface) is coated with a reflective surface to achieve reflectivity. In some embodiments, the platform or a portion thereof (e.g., the top surface) comprises a reflective material. In some embodiments, the platform or a portion thereof (e.g., the top surface) is made of a reflective material. In some embodiments, the reflective material is a white reflective material. In some embodiments, the reflective material is Teflon™ material. In some embodiments, the reflective material includes but is not limited to polytetrafluoroethylene (PTFE), Spectralon™, barium sulfate, Gold, Magnesium Oxide, or combinations thereof.

Preferably, the rotatable platform is round and larger than the size of any sample gemstone to be analyzed. In some embodiments, the platform is horizontal and remains horizontal while it is being rotated.

In some embodiments, the height of the platform is fixed. In some embodiments, the height of the platform is adjusted, either manually or via the control of a computer program.

Preferably, the platform can be raised or lowered by via the control of a computer program run by the computer unit.

In some embodiments, the platform is flat. In some embodiments, the center area on which the gemstone sample is positioned is flat and the more peripheral area on the platform is not flat. The entire platform adopts the confirmation of a flatted dome-like structure.

In some embodiments, the relative position between the platform and the illumination source can be adjusted. For example, the illumination source can be moved closer or further away from the platform.

A platform can be made of any rigid and non-transparent material such as metal, wood, dark glass, plastic or other rigid polymeric material. In some embodiments, the platform and/or area surrounding the platform are coated with non-reflective or low-reflective material.

In the broadest sense, a light source 20 includes but is not limited to the source for generating light, one or more filters, elements for conducting the generated light, and a component (e.g., a circular ring light) that emit the generated light as UV illumination. In the embodiment depicted in FIG. 3, a circular ring light 530 provides UV illumination to the sample gemstone. As disclosed herein, the source for generating light is sometimes referred to as light source. One of skill in the art would understand that the illumination component is also a part of the light source.

In some embodiments, the light generating source is separated from the ultimate illumination component, for example, it is connected with an external circular ring light (e.g., by light transmission cables) to provide the source of illumination. In such embodiments, a short-pass filter and band-pass filter for UV light selection is applied, either before or after the source of illumination reaches the circular ring light. As such, illumination ultimately provided the circular ring light has a defined ultraviolet feature; for example, having one or more wavelengths within the UV range. Such wavelengths can be any wavelength from a range of 400 nm to 10 nm, 400 nm to 385 nm, 385 nm to 350 nm, 350 nm to 300 nm, 300 nm to 250 nm, 250 nm to 200 nm, 200 nm to 150 nm, 150 nm to 100 nm, 100 nm to 50 nm, or 50 nm to 10 nm.

In one aspect, a light generating source as disclosed herein is capable of generating fluorescence excitation (e.g., at 365 nm). In another aspect, a light generating source as disclosed herein provides light illumination for gemstone outline identification. This dual-functionality is achieved by using special light source and combination of different types of light source.

In some embodiments, a tunable light source that is capable of emitting both UV and white light is used. For example, such tunable light source comprises one or more LEDs. Advantageously, such light source can be used for both outline identification and fluorescence measurements. For example, a built-in mechanism can be used to allow a user to switch between two modes of operation. In some embodiments, the light source (e.g., UV emitting LEDs) emits UV illumination at a desired wavelength (e.g., at 365 nm). For example, UV LEDs that emit UV light at a single wavelength (e.g., 365 nm or 385 nm) are available (e.g., from Hamamatsu Corporation). In some embodiments, the light source (e.g., UV emitting LEDs) emits UV illumination at a range and a desired wavelength is emitted by applying a UV-pass filter set, for example, at 365 nm.

In such embodiments, the tunable light source provides either uniform top illumination or uniform bottom illumination. For top illumination, there are no limitations on the shape and size of the light source. For example, the light source can be circular, partially circular, or non-circular at all (e.g., oval, square or triangle). There are also no limitations on the distance from the gemstone sample. For example, the tunable light source is attached to the reflective internal surface of top reflect element 60 (e.g., FIG. 2B). A combination of light sources can be used; including but not limited to one or more UV LEDs; one or more UV LEDs with an optical diffuser; one or more UV LEDs with a collimation lens; or one or more UV LEDs with a collimation lens and an optical diffuser. One of skill in the art would understand that any combination of light source and optical elements that can provide uniform illumination will be suitable as light source in an apparatus as disclosed herein.

For bottom illumination, the light source is preferably a circular ring light to be compatible with the shape of sample platform 50 (e.g., FIG. 2B). Here, elements that can generate UV illumination is arranged into a circular or near circular shape. For example, UV LEDs that emit UV light at a single wavelength (e.g., 365 nm or 385 nm) are available (e.g., from Hamamatsu Corporation). In some embodiments, the ring light has embedded within one or more UV LEDs.

In some embodiments, more than one light sources are used. At least one of the light sources is a UV light source (such as one or more UV emitting LEDs). At least another one of the light sources is a white light source. Any suitable white light source can be used, including but not limited to a fluorescence lamp, a halogen lamp, a Xe lamp, a Tungsten lamp, a metal halide lamp, a laser-induced white light (LDLS), or combinations thereof.

Many combinations can be used in such embodiments. For example, two ring lights can be used: one providing uniform UV illumination and one providing uniform daylight approximating light illumination. In this combination, in some embodiments, the light sources both provide bottom illumination. In some embodiments, one of the ring light provides bottom illumination while the other provides top illumination.

In another exemplary combination, the light source comprises a ring-shaped LED light source and a white light source. In some embodiments, the ring-shaped of UV LED is used to provide bottom illumination and the white light source provides top illumination.

In still another exemplary combination, the light source comprises a ring-shaped white light source and an LED light source. In some embodiments, the ring-shaped white light source is used to provide bottom illumination and the UV LED source provides top illumination.

As noted, the white light source comprises a daylight-approximating light source. Exemplary daylight-approximating light source includes but is not limited to one or more halogen lamps with a color balancing filter, multiple light emitting diodes arranged in a ring-like structure surrounding the platform surface, fluorescence lamp, Xe lamp, Tungsten lamp, metal halide lamp, laser-induced white light (LDLS), or combinations thereof. In some embodiments, a color balancing filter is used to create the day-light equivalent light source.

In some embodiments, when suitable, either the white light source or the UV light source can be a ring-shaped light. For example, for a UV light source, elements that can generate UV illumination is arranged into a circular or near circular shape. For example, UV light emitting diodes that emit UV light at a single wavelength (e.g., 365 nm or 385 nm) are available (e.g., from Hamamatsu Corporation). In some embodiments, the ring light has embedded within one or more UV LEDs.

In some embodiments, cables such as gooseneck light guide, flexible light guide, each containing one or more branches are used to connected the ring light with the light generating source.

The UV illumination source can adopt any shape and size that are suitable for the optical analysis of a sample gemstone. For example, the illumination source can be a point light, a round light, a ring light, an oval light, a triangular light, a square light, or any other light with suitable size and shape. In some embodiments, the light illuminating source is ring-like or circular in shape, with a diameter that is larger than that of a circular platform.

The UV illumination component provides the input light under which the sample gemstone can be analyzed. Advantageously, in an environment with no or little light interference (e.g., from the ambient light or other light), a gemstone that can generate fluorescence under UV illumination can be analyzed with great sensitivity. Here, visible fluorescence is emitted as a result of exposure to UV illumination. When the impact from UV illumination is excluded (e.g., for setting the light filter on a detector or image capture component to only visible light range), the emitted fluorescence light is compared against a zero background (e.g., no fluorescence). Here, the signal to noise ratio is very high due to the low or near zero noise level.

A modular approach to the design of the apparatus has been adopted to provide experimental flexibility. In some embodiments, the intensity of the UV illumination can be adjusted to optimize image collection.

A modular approach to the design of the apparatus has been adopted to provide experimental flexibility. In some embodiments, the intensity of the UV illumination can be adjusted to optimize image collection.

As shown in FIGS. 2A and 2B, a top reflector module can be moved over the area where a sample gemstone is position. In the closed configuration shown in FIG. 2A, the internal cavity of the top reflector module functions as a sealed and isolated sample chamber in which the sample gemstone is analyzed in a controlled environment. For example, ambient light or other light is excluded from the chamber. A user can adjust light intensity within the chamber to optimize data collection. In some embodiments, data collected include color images of the gemstone viewed from different angles.

FIGS. 5A through 5D illustrate an exemplary embodiment of the top reflector component 60. Overall, the top reflector has an external morphology that resembles that of a short cylinder, except that a portion of the cylinder is carved away to form a curved slope (see, for example, element 610 in FIGS. 5B and 5D). A portion of the slope is removed to allow access to the inside of the reflector component. For example, as shown in FIGS. 5A-5D, the lower portion of slope 610 is removed to form an opening 620. In some embodiments, the top port of opening 620 is circular in design; for example with a diameter through which a lens from the optical unit is fitted. In some embodiments, the diameter is the same as that of the telecentric lens to prevent ambient light or other light from entering the inside of the reflector. In some embodiments, the diameter is slightly larger than that of the telecentric lens such that an adaptor module is needed to prevent ambient light or other light from entering the inside of the reflector.

Inside of top reflector module 60 is reflective surface 630. This internal reflective surface is at least partially hemispherical. In some embodiments, the internal reflective surface adopts a shape that is part of the involute of a circle having a radius R. In preferred embodiments, the circle is located at the center of the platform surface and has a diameter that is larger than the sizes of the gemstones being analyzed. The shape of the involute surface is described based on the following equations:

$$x = R(\cos \theta + \theta \sin \theta)$$

$$y = R(\sin \theta - \theta \cos \theta),$$

where R is the radius of the circle and $\theta$ is an angle parameter in radians. The involute surface will reflect light toward the center circular region such that illumination of the gemstone being analyzed is optimized.

In some embodiments, the reflective surface 630 or a portion thereof comprises a reflective material. In some embodiments, the reflective surface 630 or a portion thereof is made of a reflective material. In some embodiments, the reflective material is a white reflective material. In some embodiments, the reflective material is Teflon™ material. In some embodiments, the reflective material includes but is not limited to polytetrafluoroethylene (PTFE), Spectralon™, barium sulfate, Gold, Magnesium Oxide, or combinations thereof. Additional reflective coating materials include but are not limited to a zinc salt (zinc sulfide), titanium dioxide, silicon dioxide, a magnesium salt (magnesium fluoride, magnesium sulfide).

In some embodiments with bottom UV illumination (e.g., when a ring light of UV LEDs are used), one or more reflective materials are used to reflect UV illumination towards the gemstone. In some embodiments with top UV illumination, reflective material is not needed.

As illustrated in FIG. 2B, an optical connector module 70 links the gemstone evaluation unit with the optical unit to permit data collection by image capturing device 40, whiling at the same time preventing ambient light or other light from entering the gemstone evaluation unit and interfering with data measurements.

Figure 6A:
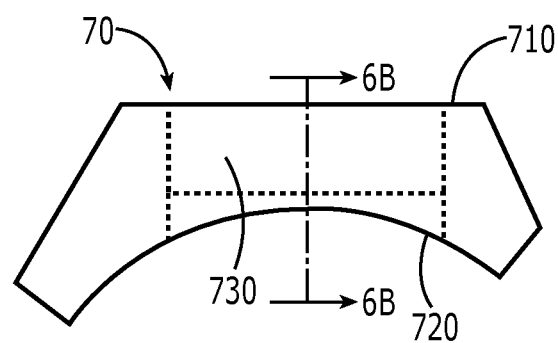
FIG. 6A depicts an exemplary embodiment of a connector module for linking a gemstone evaluation unit and an optic unit.
Figure 6B:
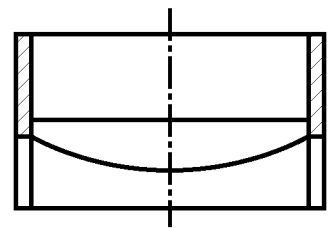
FIG. 6B depicts an exemplary embodiment of a connector module for linking a gemstone evaluation unit and an optic unit.
Figure 6C:
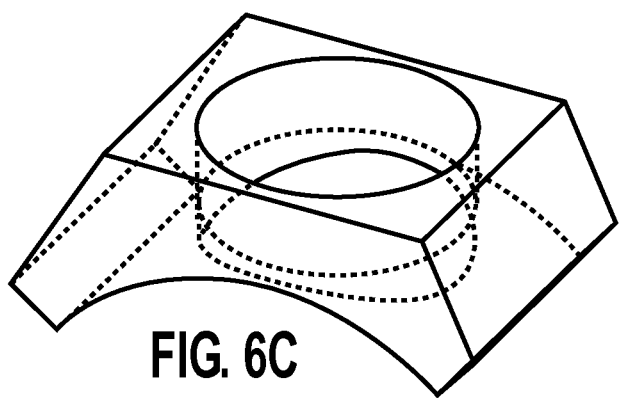
FIG. 6C depicts an exemplary embodiment of a connector module for linking a gemstone evaluation unit and an optic unit.

FIGS. 6A to 6C provide more detailed illustrations of an exemplary embodiment of an optical connector module. In this case, the connector is a lens hood for receiving the telecentric lens 30. On the side in contact with the telecentric lens, the lens hood has a flat surface 710. On the opposite side which contacts the reflector, the lens hood has a curved surface 720. In some embodiments, the curved surface 720 has a shape complementary to the curved surface 610 on the reflector.

Additionally, the connector also has an opening 730; see, FIGS. 6A, 6B, and 6C. In some embodiments, opening 730 has a configuration that accommodates the telecentric lens while preventing interference from ambient light or other light. For example, opening 730 depicted in FIGS. 6A-6B has a cylindrical opening that is not uniform in size. For example, the diameter of the cylindrical opening on the lens-contacting side is smaller than the diameter of the cylindrical opening on the reflector-contacting side.

A lens hood or other optical connector module allows integration of two different functional components. It is designed such that no or very little ambient light or other light enters the sample chamber. In some embodiments, additional elements such as a sealing tape can be used to exclude ambient light or other light.

Another main functional component of the system is an optical unit through which data of the gemstones being analyzed. The optical unit provides a sample chamber that enables the collection of a visible-light spectrum from an area containing a sample gemstone while excluding light from outside the chamber. Optical measurement such as an image is captured of the area containing the sample gemstone and, possibly through analysis of the detailed structure of the images, to provide some insight into the reasons for certain stones that previously had anomalous grading results.

Exemplary embodiments disclosed herein include but are not limited to two important functional modules in the optical unit a telecentric lens 30 and an image capturing component 40 such as a color camera. One of skill in the art would understand that additional components can be present to facilitate data collection.

A telecentric lens is used to provide an image of the illuminated gemstone to the image capturing component. Telecentricity refers to a unique optical property where the chief rays (oblique rays which pass through the center of the aperture stop) through a certain lens design are collimated and parallel to the optical axis in image and/or object space. A telecentric lens is a compound lens which has its entrance or exit pupil at infinity. Advantageously, a telecentric lens provides constant magnification (object size does not change) over a range of working distances, virtually eliminating perspective angle error. For many applications, this means that object movement does not affect image magnification, allowing for highly accurate measurements in gauging applications. This level of accuracy and repeatability cannot be obtained with standard lenses. The simplest way to make a lens telecentric is to put the aperture stop at one of the lens's focal points.

There are three types of telecentric lens. An entrance pupil at infinity makes a lens object-space telecentric. An exit pupil at infinity makes the lens image-space telecentric. If both pupils are at infinity, the lens is double telecentric.

Telecentric lens with high depth of field are used in the system disclosed herein. In some embodiments, a telecentric lens used is an object-space telecentric lens. In some embodiments, a telecentric lens is a double telecentric lens. In preferred embodiments, zoom should be fixed for all images collection for a given gemstone stone to further ensure consistency.

Advantageously, the present apparatus and system do not require that the sample gemstone be placed at the center of the platform surface. In addition, a telecentric lens does not discriminate the size of the sample gemstones. The same telecentric lens can be used to collection images for a very small gemstone and a significantly larger gemstone.

The optical unit further comprises an image capture component or a detector such as a digital camera. In order to only capture fluorescence emitted from the gemstones, a filter is applied to exclude interference from UV illumination.

In some embodiments, image capturing component 40 comprises one or more photodiode arrays of a CCD (charge coupled device). In some embodiments, image capturing component 40 comprises one or more CMOS (complementary metal oxide semiconductor) image sensors. In some embodiments, image capturing component 40 comprises a combination of one or more photodiode arrays with CMOS sensors. In some embodiments, image capturing component 40 is a CCD digital camera, such as a color digital camera. When images from different fluorescence grading apparatuses are analyzed, more consistent results can be obtained if the apparatuses use the same type of detection methods; for example, all CCD arrays, all CMOS sensors, or the same combination of both types.

For more accurate analytical results, the resolution limit for the digital images collected is 600 pixel×400 pixel or above. In some embodiments, each pixel has an 8-bit value (e.g., 0 to 255) for each color component. The Analog to Digital Converter (ADC) of the digital camera is 8-bit or above in order to efficiently process the information embedded in the pixels without little or no loss of image quality. In some embodiments, the ADC is 10-bit or above according to the dynamic range of image capturing component. In some embodiments, the ADC is between 10-bit and 14-bit.

In some embodiments, the color components in a pixel include but not limited to red (R), green (G) and blue (B). In some embodiments, the color components in a pixel include but not limited to) cyan (C), magenta (M), yellow (Y), and key (black or B). In some embodiments, the color components in a pixel include but not limited to red (R), yellow (Y) and blue (B).

Image View Angle:

As depicted in FIG. 4, an image capturing device the optical unit (or telecentric lens 30 or both) is positioned at a pre-determined angle (alpha, also referred to as the image view angle) relative to the platform surface. In some embodiments, the image view angle is 65 degree or smaller, 60 degree or smaller, 56 degree or smaller, 52 degree or smaller, 50 degree or smaller, 48 degree or smaller, 46 degree or smaller, 44 degree or smaller, 42 degree or smaller, 40 degree or smaller, 39 degree or smaller, 38 degree or smaller, 37 degree or smaller, 36 degree or smaller, 35 degree or smaller, 34 degree or smaller, 33 degree or smaller, 32 degree or smaller, 31 degree or smaller, 30 degree or smaller, 29 degree or smaller, 28 degree or smaller, 27 degree or smaller, 26 degree or smaller, 25 degree or smaller, 24 degree or smaller, 23 degree or smaller, 22 degree or smaller, 21 degree or smaller, 20 degree or smaller, 19 degree or smaller, 18 degree or smaller, 17 degree or smaller, 16 degree or smaller, 15 degree or smaller, 14 degree or smaller, 13 degree or smaller, 12 degree or smaller, 11 degree or smaller, or 10 degree or smaller. In some embodiments, the image view angle is between about 10 degree and about 45 degree. For consistency, the image view angle for a given gemstone will remain constant when images are collected.

Image Rotational Angle:

Also as illustrated in FIG. 4, the relative rotational position between the imaging capturing component and a pre-defined location on the platform (e.g., point 540) can be described by an image rotational angle beta. For example, the image capturing component and the platform surface can be rotated relative to each other such that the image rotational angle is varied by a set angular variation between consecutive images. For example, the angular variation between two consecutive images can be 0.5 degree or smaller, 1 degree or smaller, 1.5 degree or smaller, 2 degree or smaller, 3 degree or smaller, 4 degree or smaller, 5 degree or smaller, 6 degree or smaller, 7 degree or smaller, 8 degree or smaller, 9 degree or smaller, 10 degree or smaller, 12 degree or smaller, 15 degree or smaller, 18 degree or smaller, 20 degree or smaller, 24 degree or smaller, 30 degree or smaller, 45 degree or smaller, 60 degree or smaller, 90 degree or smaller, or 180 degree or smaller. It will be understood that the angular rotational variation can be set at any number.

It will also be understood that the platform and image capturing component can be rotated relative to each other for a total rotational angle of any value, not limited to a 360 degree full rotation. In some embodiments, data (e.g., color images) are collection for a rotation less than a 360 degree full rotation. In some embodiments, data (e.g., color images) are collection for a rotation more than a 360 degree full rotation.

It is possible to change angular rotational variation when collecting a set of images for the same sample gemstone. For example, the angular different between image 1 and image 2 can be 5 degrees, but the different between image 2 and 3 can be 10 degrees. In preferred embodiments, angular difference between consecutive images remains constant within the same set of images for the same sample gemstone. In some embodiments, only one set of images is collection for a given sample gemstone. In some embodiments, multiple sets of images are collected for the same gemstone where angular differences remain constant within each set but are different from each other. For example, a first set of images is collected by varying the rational image angle by 12 degree for consecutive images, while a second set of images is collected by varying the rational image angle by 18 degree for consecutive images.

The number of images collected for a given sample gemstone varies depending on the characteristics of the gemstone. Exemplary characteristics include but are not limited to shape, cut, size, color and etc.

Visible-light spectra from an area on the platform surface that contains the sample gemstone is selectively collected. In some embodiments, multiple color images are collected for each gemstone. In some embodiments, multiple non-color images are collected for each gemstone. Color images are advantageous for determining, for example, the color grade of a cut diamond.

In some embodiments, as will be discussed further in sections that follow, images captures by the CCD camera will be processed in order to identify regions of differing intensity of color or fluorescence. Furthermore, colorimetric calculations can be performed on these different areas using the red, green and blue signals from the camera pixels. In some embodiment, such calculations will be sufficiently accurate to give a fluorescence grade. In some embodiment, such calculations will be sufficiently accurate to provide a color distribution across the diamond and the comparison of these color calculations with that obtained from the measured spectrum can help identify diamonds that are likely to give anomalous results.

In some embodiments, the fluorescence grade is determined based on color values computed from the entire sample gemstone. In some embodiments, the fluorescence grade is determined based on color values computed from color area of the sample gemstone.

Resolution and capacity of a detector can be determined by the number and size of the pixel in the detector arrays. In general, the spatial resolution of the digital image is limited by the pixel size. Unfortunately while reducing pixel size improves spatial resolution this comes at the expense of signal to noise ratio (SNR or signal/noise ratio). In particular, signal-to-noise ratio is improved when image sensor pixel size is increased or image sensor is cooled. At the same time, size of the image sensor is increased if image sensor resolution is kept the same. Detectors of higher quality (e.g., better digital cameras) have a large image sensor and a relatively large pixel size for good image quality.

In some embodiments, a detector of the present invention has a pixel size of 1 µm2 or smaller; 2 µm2 or smaller; 3 µm2 or smaller; 4 µm2 or smaller; 5 µm2 or smaller; 6 µm2 or smaller; 7 µm2 or smaller; 8 µm2 or smaller; 9 µm2 or smaller; 10 µm2 or smaller; 20 µm2 or smaller; 30 µm2 or smaller; 40 µm2 or smaller; 50 µm2 or smaller; 60 µm2 or smaller; 70 µm2 or smaller; 80 µm2 or smaller; 90 µm2 or smaller; 100 µm2 or smaller; 200 µm2 or smaller; 300 µm2 or smaller; 400 µm2 or smaller; 500 µm2 or smaller; 600 µm2 or smaller; 700 µm2 or smaller; 800 µm2 or smaller; 900 µm2 or smaller; 1,000 µm2 or smaller; 1,100 µm2 or smaller; 1,200 µm2 or smaller; 1,300 µm2 or smaller; 1,400 µm2 or smaller; 1,500 µm2 or smaller; 1,600 µm2 or smaller; 1,700 µm2 or smaller; 1,800 µm2 or smaller; 1,900 µm2 or smaller; 2,000 µm2 or smaller; 2,100 µm2 or smaller; 2,200 µm2 or smaller; 2,300 µm2 or smaller; 2,400 µm2 or smaller; 2,500 µm2 or smaller; 2,600 µm2 or smaller; 2,700 µm2 or smaller; 2,800 µm2 or smaller; 2,900 µm2 or smaller; 3,000 µm2 or smaller; 3,100 µm2 or smaller; 3,200 µm2 or smaller; 3,300 µm2 or smaller; 3,400 µm2 or smaller; 3,500 µm2 or smaller; 3,600 µm2 or smaller; 3,700 µm2 or smaller; 3,800 µm2 or smaller; 3,900 µm2 or smaller; 4,000 µm2 or smaller; 4,100 µm2 or smaller; 4,200 µm2 or smaller; 4,300 µm2 or smaller; 4,400 µm2 or smaller; 4,500 µm2 or smaller; 4,600 µm2 or smaller; 4,700 µm2 or smaller; 4,800 µm2 or smaller; 4,900 µm2 or smaller; 5,000 µm2 or smaller; 5,100 µm2 or smaller; 5,200 µm2 or smaller; 5,300 µm2 or smaller; 5,400 µm2 or smaller; 5,500 µm2 or smaller; 5,600 µm2 or smaller; 5,700 µm2 or smaller; 5,800 µm2 or smaller; 5,900 µm2 or smaller; 6,000 µm2 or smaller; 6,500 µm2 or smaller; 7,000 µm2 or smaller; 7,500 µm2 or smaller; 8,000 µm2 or smaller; 8,500 µm2 or smaller; 9,000 µm2 or smaller; or 10,000 µm2 or smaller. In some embodiments, the pixel size is larger than 10,000 µm2; for example, up to 20,000 µm2; 50,000 µm2; or 100,000 µm2.

In some embodiments, exposure time to the detector can be adjusted to optimize image quality and to facilitate the determination of a grade for an optical quality of the gemstone, such as color or fluorescence level. In some embodiments, fluorescence emission is quite weak and consequently long exposure time is needed for assessing fluorescence quality. For example, the exposure time to a CCD detector can be 0.1 millisecond (ms) or longer, 0.2 ms or longer, 0.5 ms or longer, 0.8 ms or longer, 1.0 ms or longer, 1.5 ms or longer, 2.0 ms or longer, 2.5 ms or longer, 3.0 ms or longer, 3.5 ms or longer, 4.0 ms or longer, 4.5 ms or longer, 5.0 ms or longer, 5.5 ms or longer, 6.0 ms or longer, 6.5 ms or longer, 7.0 ms or longer, 7.5 ms or longer, 8.0 ms or longer, 8.5 ms or longer, 9.0 ms or longer, 9.5 ms or longer, 10.0 ms or longer, 15.0 ms or longer, 20.0 ms or longer, 25.0 ms or longer, 30.0 ms or longer, 35.0 ms or longer, 40.0 ms or longer, 45.0 ms or longer, 50.0 ms or longer, 55.0 ms or longer, 60.0 ms or longer, 65.0 ms or longer, 70.0 ms or longer, 75.0 ms or longer, 80.0 ms or longer, 85.0 ms or longer, 90.0 ms or longer, 95.0 ms or longer, 100.0 ms or longer, 105.0 ms or longer, 110.0 ms or longer, 115.0 ms or longer, 120.0 ms or longer, 125.0 ms or longer, 130.0 ms or longer, 135.0 ms or longer, 140.0 ms or longer, 145.0 ms or longer, 150.0 ms or longer, 175.0 ms or longer, 200.0 ms or longer, 225.0 ms or longer, 250.0 ms or longer, 275.0 ms or longer, 300.0 ms or longer, 325.0 ms or longer, 350.0 ms or longer, 375.0 ms or longer, 400.0 ms or longer, 425.0 ms or longer, 450.0 ms or longer, 475.0 ms or longer, 500.0 ms or longer, 550.0 ms or longer, 600.0 ms or longer, 650.0 ms or longer, 700.0 ms or longer, 750.0 ms or longer, 800.0 ms or longer, 850.0 ms or longer, 900.0 ms or longer, 950.0 ms or longer, 1 s (second) or longer, 1.1 s or longer, 1.2 s or longer, 1.3 s or longer, 1.4 s or longer, 1.4 s or longer, 1.5 s or longer, 1.6 s or longer, 1.7 s or longer, 1.8 s or longer, 1.9 s or longer, 2 s or longer, 2.5 s or longer, 3 s or longer. It is understood that the time of exposure can vary with respect to, for example, light source intensity.

In another aspect, the methods and systems disclosed herein are used to detect or evaluate changes of fluorescence properties of a sample gemstone over time. For example, the color of the fluorescence of a gemstone may change over time. Also, the intensity of the fluorescence of a gemstone may change over time.

In such embodiments, multiple sets or pluralities of images (e.g., color images) are collected of a gemstone over a period of time. For example, using the system disclosed herein, each set of image is collected automatically over multiple image angles. There is no limitation as to how much sets of image can be collected over time, for example, two or more sets of images; three or more sets of images; four or more sets of images; five or more sets of images; six or more sets of images; seven or more sets of images; eight or more sets of images; nine or more sets of images; 10 or more sets of images; 15 or more sets of images; 20 or more sets of images; 30 or more sets of images; 50 or more sets of images; or 100 or more sets of images can be collected.

In some embodiments, all sets of images are collected of the same gemstone by applying the same system configuration; for example, using the same camera, same image angle, same reflector, same platform and etc.

Among the multiple sets of images, two consecutive sets of image are separately for a time gap ranging from minutes to hours or even days, depending on the nature of the color change of the stone. The duration of the time gap is determined by how quickly color changes may take place in the sample stone. There is no limitation as to how long or how short the time gap can be. For example, the time gap can be two minutes or shorter; five minutes or shorter; 10 minutes or shorter; 20 minutes or shorter; 30 minutes or shorter; 60 minutes or shorter; 2 hours or shorter; 5 hours or shorter; 12 hours or shorter; 24 hours or shorter; 2 days or shorter; 5 days or shorter; or 10 days or shorter.

In some embodiments, calculations are done for each set of images to assign a fluorescence grade for the sample gemstone. Fluorescence grades from multiple sets of images are then compared to determine fluorescence change over time.

In another aspect, also provided herein is a data analysis unit, including both a hardware component (e.g., computer) and a software component.

Figure 8:
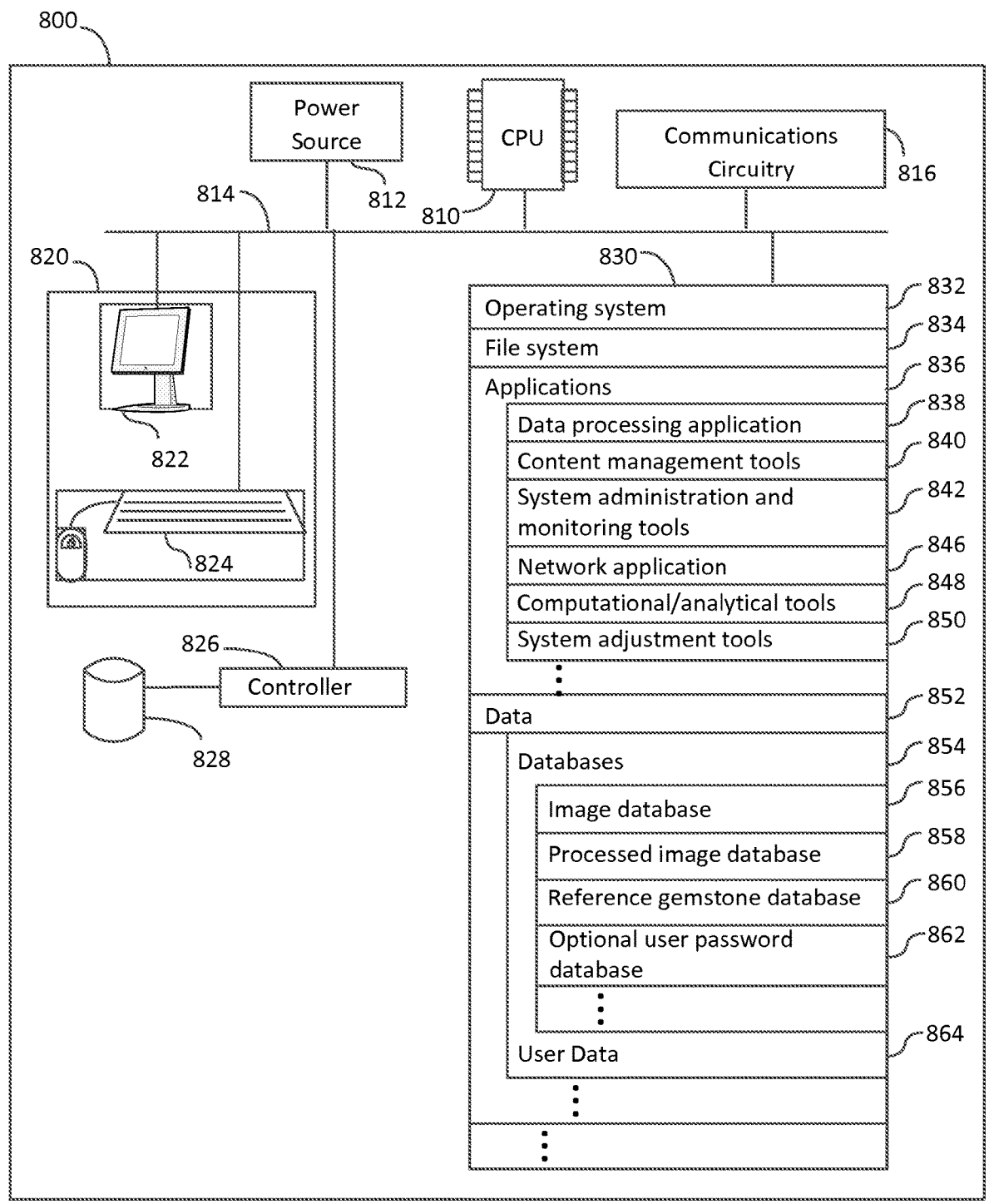
FIG. 8 depicts an exemplary organization of a computer system.

The data analysis unit stores, converts, analyzes, and processes of the images collected by the optical unit. The computer unit controls various components of the system, for example, rotation and height adjustment of the platform, adjustment of the intensity and exposure time of the illumination source. The computer unit also controls the zoom, adjusts relative position of the optic unit to the gemstone platform, FIG. 8 illustrates an exemplary computer unit 800. In some embodiments, a computer unit 800 comprises a central processing unit 810, a power source 812, a user interface 820, communications circuitry 816, a bus 814, a non-volatile storage controller 826, an optional non-volatile storage 828, and a memory 830.

Memory 830 may comprise volatile and non-volatile storage units, for example random-access memory (RAM), read-only memory (ROM), flash memory and the like. In some embodiments, memory 830 comprises high-speed RAM for storing system control programs, data, and application programs, e.g., programs and data loaded from non-volatile storage 828. It will be appreciated that at any given time, all or a portion of any of the modules or data structures in memory 830 can, in fact, be stored in memory 828.

User interface 820 may comprise one or more input devices 824, e.g., keyboard, key pad, mouse, scroll wheel, and the like, and a display 822 or other output device. A network interface card or other communication circuitry 816 may provide for connection to any wired or wireless communications network. Internal bus 814 provides for interconnection of the aforementioned elements of the computer unit 30.

In some embodiments, operation of computer unit 800 is controlled primarily by operating system 828, which is executed by central processing unit 810. Operating system 382 can be stored in system memory 830. In addition to operating system 382, a typical implementation of system memory 830 may include a file system 834 for controlling access to the various files and data structures used by the present invention, one or more application modules 836, and one or more databases or data modules 852.

In some embodiments in accordance with the present invention, applications modules 836 may comprise one or more of the following modules described below and illustrated in FIG. 8.

Data Processing Application 838:

In some embodiments in accordance with the present invention, a data processing application 838 receives and processes optical measurements shared between the optical unit and data analysis unit. In some embodiments, data processing application 838 utilizes an algorithm to determine the portion of the image that corresponds to the sample gemstone and eliminates the irrelevant digital data. In some embodiments, data processing application 838 converts each pixel of the digital images into individual color components.

Content Management Tools 840:

In some embodiments, content management tools 840 are used to organize different forms of data 852 into multiple databases 854, e.g., an image database 856, a processed image database 858, a reference gemstone database 860, and an optional user password database 862. In some embodiments in accordance with the present invention, content management tools 840 are used to search and compare any of the databases hosted on computer unit 30. For example, images of the same sample gemstone taken at different time can be organized into the same database. In addition, information concerning the sample gemstone can be used to organize the image data. For example, images of diamonds of the same cut may be organized into the same database. In addition, images of diamonds of the same source may be organized into the same database.

The databases stored on the computer unit 800 comprise any form of data storage system including, but not limited to, a flat file, a relational database (SQL), and an on-line analytical processing (OLAP) database (MDX and/or variants thereof). In some specific embodiments, the databases are hierarchical OLAP cubes. In some embodiments, the databases each have a star schema that is not stored as a cube but has dimension tables that define hierarchy. Still further, in some embodiments, the databases have hierarchy that is not explicitly broken out in the underlying database or database schema (e.g., dimension tables are not hierarchically arranged).

In some embodiments, content management tools 840 utilize a clustering method for determining grading characteristics.

System Administration and Monitoring Tools 842:

In some embodiments in accordance with the present invention, the system administration and monitoring tools 842 administer and monitor all applications and data files of computer unit 30. System administration and monitoring tools 842 control which users, servers, or devices have access to computer unit 30. In some embodiments, security administration and monitoring is achieved by restricting data download or upload access from computer unit 800 such that the data is protected against malicious access. In some embodiments, system administration and monitoring tools 842 use more than one security measure to protect the data stored on computer unit 30. In some embodiments, a random rotational security system may be applied to safeguard the data stored on remote computer unit 30.

Network Application 846:

In some embodiments, network applications 846 connect computer unit 800 to network and thereby to any network devices. In some embodiments, a network application 846 receives data from intermediary gateway servers or one or more remote data servers before it transfers the data to other application modules such as data processing application 838, content management tools 840, and system administration and monitoring tools 842.

Computational and Analytical Tools 848:

Computational and analytical tools 848 can apply any available methods or algorithm to analyze and process images collected from a sample gemstone.

System Adjustment Tools 850:

System adjustment tools 850 controls and modifies configurations of various components of the system. For example, system adjustment tools 850 can switch between different masks, alter the size and shape of an adjustable mask, adjust zoom optics, set and modify exposure time, and etc.

Data Module 852 and Databases 854:

In some embodiments, each of the data structures stored on computer unit 800 is a single data structure. In other embodiments, any or all such data structures may comprise a plurality of data structures (e.g., databases, files, and archives) that may or may not all be stored on computer unit 30. The one or more data modules 852 may include any number of databases 852 organized into different structures (or other forms of data structures) by content management tools 840.

In addition to the above-identified modules, various database 854 may be stored on computer unit 800 or a remote data server that is addressable by computer unit 800 (e.g., any remote data server that the computer unit can send information to and/or retrieve information from). Exemplary databases 854 include but are not limited to image database 856, processed image database 858, reference gemstone database 860, optional member password dataset 862, and gemstone data 864.

Image database 856 is used to store images of gemstones before they are analyzed. Processed image database 858 is used to store processed gemstone images. In some embodiments, processed image database 858 also stored data that are converted from processed images. Examples of converted data include but are not limited to individual color components of pixels in an image, a two or three dimensional map representing color distribution of the pixels in an image; computed L*, C*, a or b values of pixels in an image; average of L*, C*, a or b values for one or more images.

Reference Gemstone Database 860:

Data of existing or known reference, or master gemstones (e.g., grade values or L*, C*, a or b values) are stored in reference gemstone database 860. In some embodiments, information of the known reference, or master gemstones is used as standards for determining the grade values, or L*, C*, a or b values of an unknown gemstone samples. The optical quality, such as color or fluorescence grade, has already been determined for the known reference, or master gemstones. For example, optical measurements of a sample diamond of brilliant cut are used to compute a value of L*, C*, a or b, which is then compared with the values of L*, C*, a or b of a plurality of known reference, or master diamond of the same cut. The grade of the sample diamond will be determined by the most closely match reference gemstone. In preferred embodiments, the reference gemstones are of the same or similar size or weight as the sample gemstone.

Optional User Password Database 862:

In some embodiments, an optional password database 862 is provided. Password and other security information relating to users of the present system can be created and stored on computer unit 800 where passwords of the users are stored and managed. In some embodiments, users are given the opportunity to choose security settings.

In one aspect, provided herein are methods for system calibration, data collection, data processing and analysis. For example, color digital images of gemstones are obtained, processed and computed to render one or more values for assessing and grading quality of cut gemstones such as diamonds.

Not all gemstones emit fluorescence upon UV exposure. Even for gemstones that do emit fluorescence upon UV exposure, fluorescence levels are very unlikely to be uniform because fluorescent material within a gemstone is usually not uniformly distributed. Further, not all parts of a gemstone can emit fluorescence. An important aspect of fluorescence grading is to precisely identify regions within which fluorescence is emitted and to focus data analysis within such regions to improve accuracy.

For fluorescence analysis, at least two sets of test data are used. For example, for a given sample gemstone under the same conditions (e.g., at a set image view angle and set image rotational angle), at least two images are captured: one image under regular non-UV illumination (e.g., under a visible daylight approximating light source), and another image under UV illumination (e.g., a fluorescence or fluorescent image, also referred to as a UV image). In some embodiments, the set of images captured under regular non-UV illumination is used to extrapolate outline masks. In some embodiments, the set of images captured under UV illumination is used to extrapolate area of fluorescence (e.g., FIGS. 7C and 7D). In contrast, for color analysis, one set of test data is used. For example, a sample gemstone is under the same illumination conditions (e.g., under a daylight approximating light source) while multiple color images of the sample gemstone are captured with a telecentric lens at the same image view angle while changing the image rotational angle at a set interval.

Figure 7A:
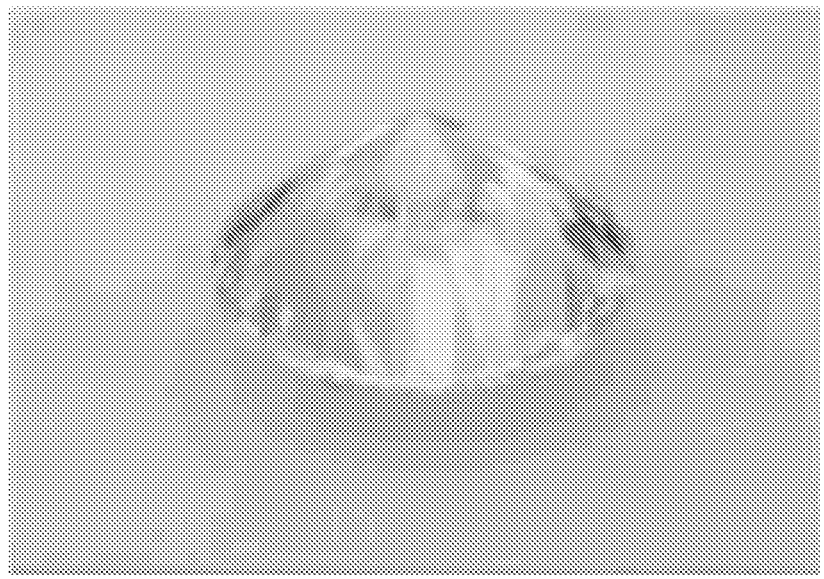
FIG. 7A depicts an exemplary embodiment, showing a RBC diamond being illuminated by daylight approximating light source.
Figure 7B:
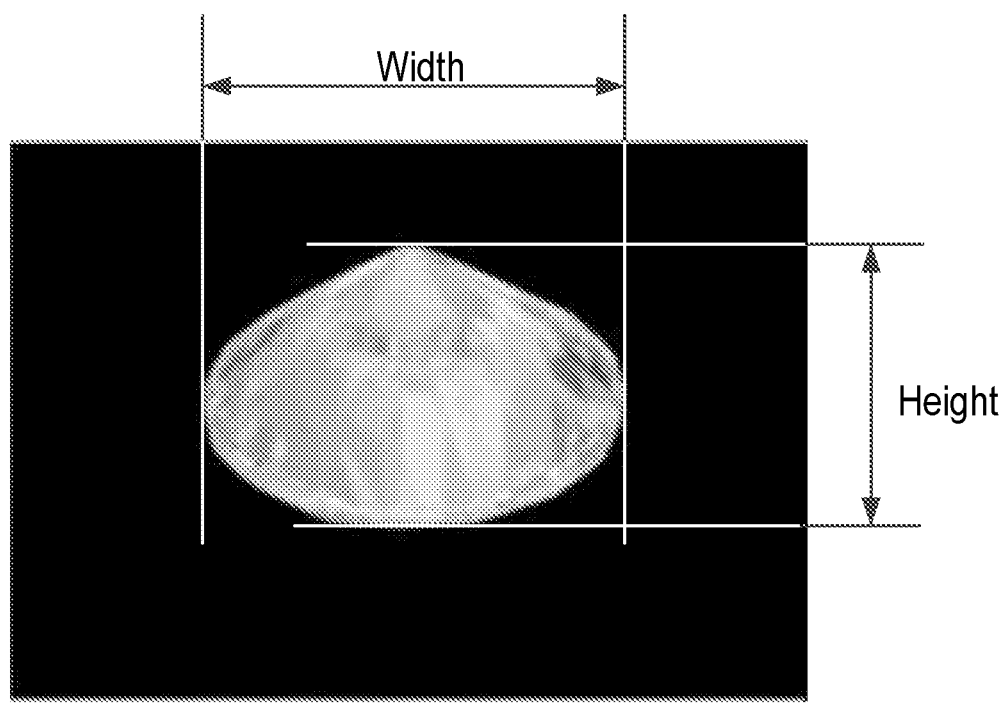
FIG. 7B depicts an exemplary embodiment, showing an image of a RBC diamond being illuminated by daylight approximating light source after an outline mask is applied.

FIGS. 7A and 7B illustrate images of a diamond in which the background white color has been masked to highlight the presence of the diamond. As illustrated in FIG. 7B, the dark area surrounding the diamond forms an outline mask. In some embodiments, an outline mask corresponds to the physical boundaries or edges of a sample gemstone, as viewed at a given image view angle and a given image rotational angle. Consequently, the opening of the outline mask encompasses a full image or the entire area of the sample gemstone at the given image view angle and image rotational angle. As illustrated in the method of analysis section, such outline masks can be defined for each image to isolate the region of analysis and to extract measurements such as width and height.

Figure 7C:
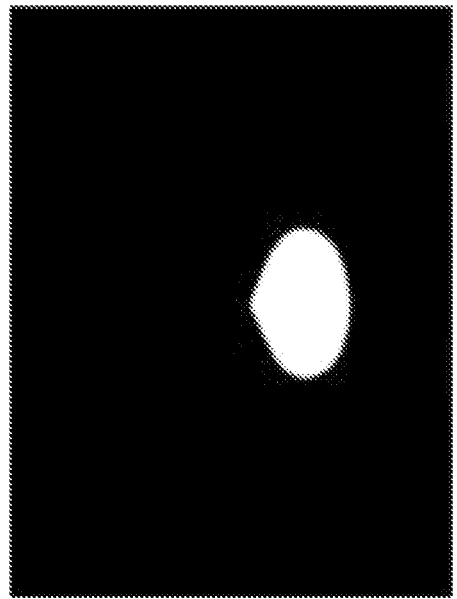
FIG. 7C depicts an exemplary embodiment, showing extraction of an outline mask.
Figure 7C:
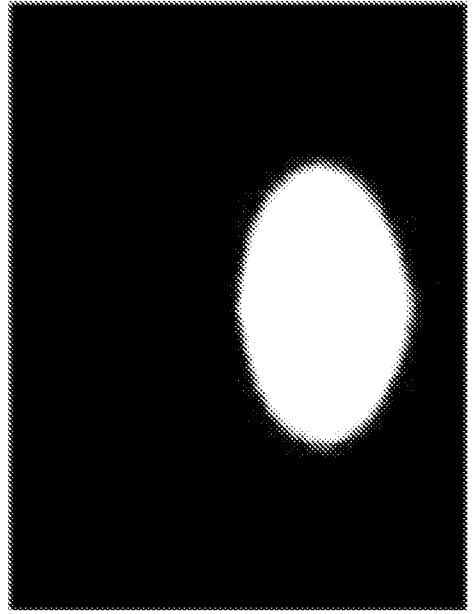
Figure 7D:
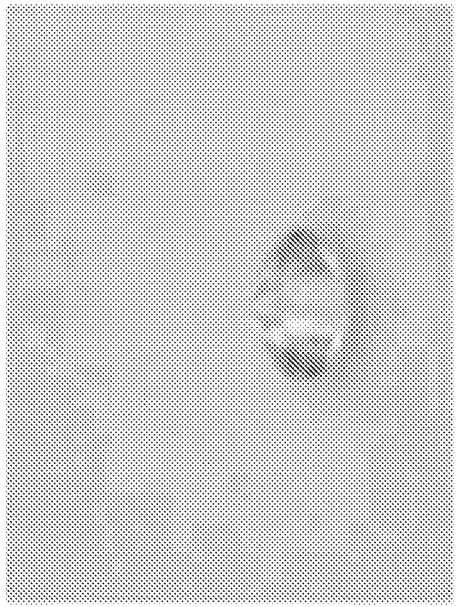
FIG. 7D depicts an exemplary embodiment, showing extraction of an apparent fluorescence area.
Figure 7D:
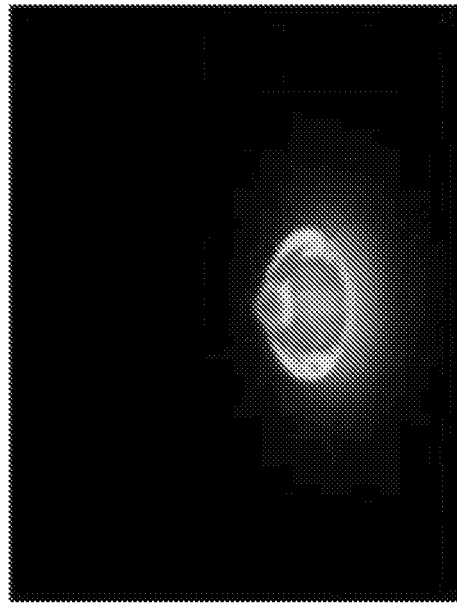

FIG. 7C depicts a gemstone illuminated under a visible light source, before (a) and after (b) outline extraction. As illustrated, the resulting outline mask corresponds to the physical size of the diamond in two dimensions under the specific image capturing conditions. FIG. 7D depicts a gemstone illuminated under a UV light source in a fluorescence image, before (a) and after (b) fluorescence extraction.

Here, it is important to understand that the area appearing to be fluorescent in a fluorescence image (i.e., the apparent fluorescence area) can be different in size (e.g., larger) than the area (or areas) within a gemstone that is capable of emitting fluorescence, because fluorescence emission when captured in an image can extend from the area emitting fluorescence. As shown in (b), the apparent fluorescence area is in fact larger than the physical size of the diamond itself due to fluorescent light being reflected from a sample platform. As a result, the apparent fluorescence area is much larger than the opening of the outline mask, as illustrated in the comparison between FIG. 7C(b) and FIG. 7D(b). In some embodiments, the outline mask is used to calculate fluorescence intensity; for example, as represented by the parameter L according to Commission Internationale de l'Eclairage (CIE or the International Commission on Illumination). Here, the entire area of the gemstone will be assessed to accurately quantitate the overall fluorescence emission level of the gemstone.

A fluorescence mask is used to define the area within the gemstone that will be subject to further analysis or calculation. In the scenario illustrated in FIGS. 7C and 7D, the apparent fluorescence area is much larger than the physical size of the gemstone (e.g., as represented by the opening of an outline mask), which suggests that the apparent fluorescence area includes areas that do not correspond to any part of a gemstone. To eliminate inaccuracies, any fluorescence beyond the physical boundaries of the gemstone is removed from further data analysis. Only fluorescent measurements from within the boundaries of a gemstone will be subject to further calculation and analysis to provide assessment of the fluorescence light emitted from the gemstone. When fluorescence is emitted from the entire gemstone and the apparent fluorescence area covers the entire gemstone, the fluorescence mask is identified by overlaying the apparent fluorescence area; e.g., FIG. 7D(b), onto the outline mask for the gemstone; e.g., FIG. 7C(b). Any area in the apparent fluorescence area that is outside of the boundaries defined by the outline mask will be eliminated. The remaining portion of the apparent fluorescence area corresponds to the fluorescence mask. In fact, fluorescence mask is calculated by FIG. 7C (b)×FIG. 7D (b). Could you change the above description accordingly? Under the above description, inhomogeneous strong fluorescence diamond cannot be covered.

In other gemstones, an apparent fluorescence area can also be smaller than the physical boundaries of the gemstone, as defined by an outline mask and shown in FIGS. 7E and 7F. FIG. 7E illustrates an outline extraction from (a) to (b), similar to that of FIG. 7C. In FIG. 7F, fluorescence is emitted from only limited areas within the gemstone. The areas are small and disconnected. After fluorescence extraction is applied, an apparent fluorescence area is obtained as indicated in FIG. 7F(b). In this case, the apparent fluorescence area also contains patches of disconnected smaller areas. The overall apparent fluorescence area is much smaller than the outline mask shown in FIG. 7E.

In the scenario illustrated in FIGS. 7E and 7F, the apparent fluorescence area is much smaller than the physical size of the gemstone (e.g., as represented by the opening of an outline mask). In addition, fluorescence in the apparent fluorescence area is non-contiguous, which means that non-emitting areas have been excluded from the apparent fluorescence area. To eliminate inaccuracies, in some embodiments, a fluorescence mask with an opening matching the smaller apparent fluorescence area will be used to define the area within the gemstone for further analysis. Once again, the fluorescence mask is identified by overlaying the apparent fluorescence area; e.g., FIG. 7F(b), onto the outline mask for the gemstone; e.g., FIG. 7E(b). Any area in the apparent fluorescence area that is outside of the boundaries defined by the outline mask will be eliminated. The remaining portion of the apparent fluorescence area corresponds to the fluorescence mask. Only fluorescent measurements from within the opening of the fluorescence mask will be subject to further calculation and analysis to provide assessment of the fluorescence light emitted from the gemstone.

In some embodiments, the fluorescence mask comprises a contiguous opening; see e.g., (b) of FIG. 7C. In some embodiments, the fluorescence mask comprises a non-contiguous opening; see, e.g., (b) FIG. 7F. In some embodiments, the total opening area of the fluorescence mask corresponds to the physical size of the gemstone. In some embodiments, the total opening area of the fluorescence mask is much smaller than the physical size of the gemstone.

Figure 9A:
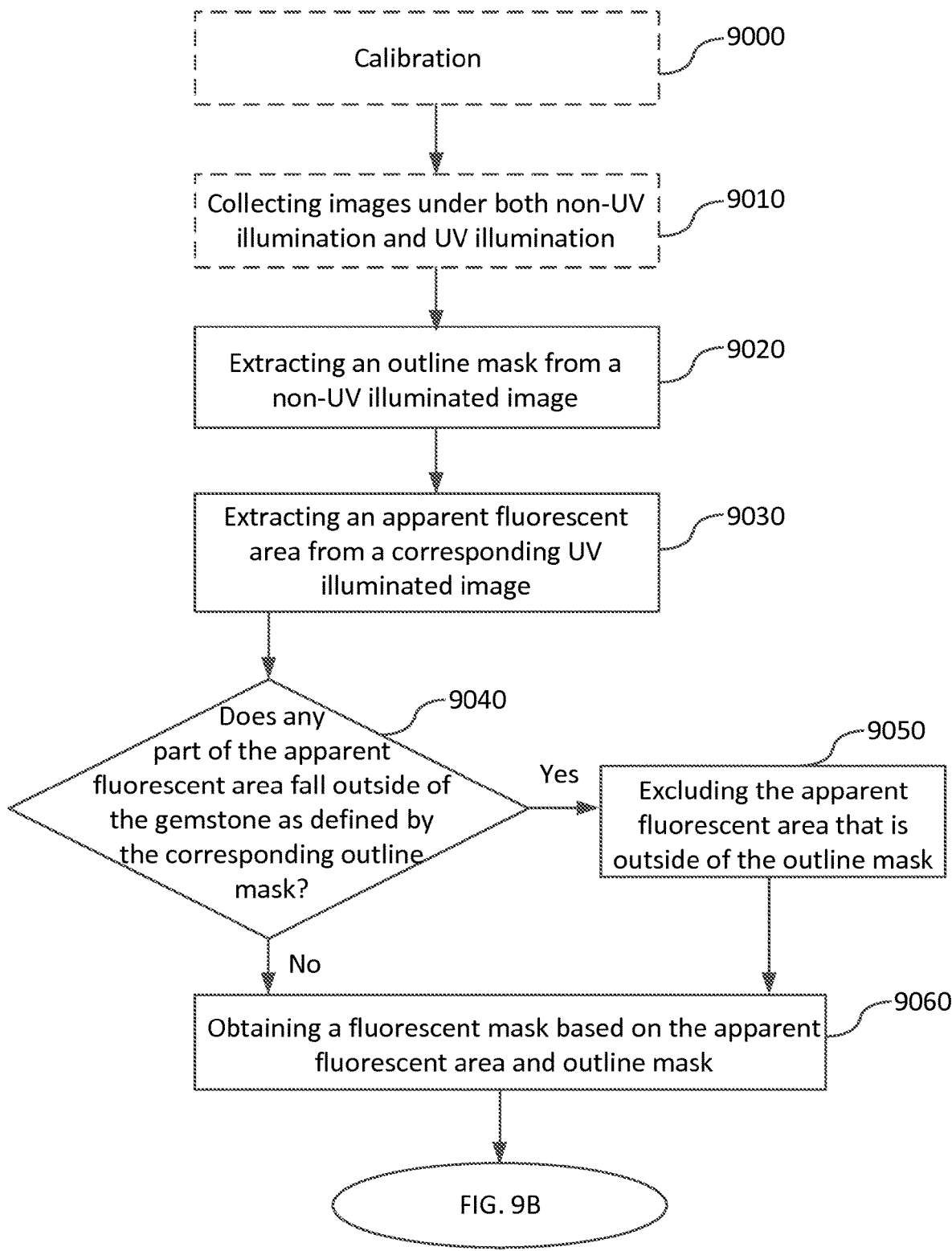
FIG. 9A depicts an exemplary process for a data collection and analysis.

An exemplary process based on the apparatus and system disclosed herein is outlined in FIG. 9A. One of skill in the art would understand the steps provided are exemplary and can be applied in any order or used in any possible combination.

At step 9000, system calibration is performed. For example, in order to have reproducible results and cancel out the fluctuation of non-UV light source, white balance of an image capture component such as a color camera is adjusted. At this step, the pixel gains of individual color components (e.g., RGB) are adjusted such that the background image of the platform surface becomes white. Background adjustment is done with a bare platform surface; i.e., the sample gemstone is not yet positioned on the platform surface. Preferably, the background adjustment is done after the light source has stabilized. In some embodiments, the background adjustment is done with a short time period before images of a sample gemstone are collected. In some embodiments, the background adjustment is done after the light source has stabilized and soon before gemstone image collection. White background adjustment is performed when the top reflector module 60 is in closed configuration. The top reflector module is then opened and a user can place a sample gemstone at the center of the platform surface. Care is taken such that the platform surface, illumination and other conditions and settings in the sample chamber and for the optical unit remain the same before and after the sample gemstone is placed.

Fluorescence measures the visible light emitted by fluorescent material (e.g., fluorophores) when it receive input energy from the UV illumination. It will be generally understood that the more intense the UV illumination, the more strongly the fluorescent material will emit visible light.

In some embodiments, intensity of the input UV illumination is adjusted to optimize fluorescence measurements. For example, a power meter (e.g., the PM160T thermal sensor power meter from Thorlabs) is used to measure light intensity from the UV light source. UV intensity is adjusted to the same intensity level in order to provide reproducible fluorescence measurement results.

At step 9010, color images of a sample gemstone are captured at different image rotational angles while maintaining the image view angle constant. At each image rotational angle, at least two images will be captures of the gemstone: a regular image for when the gemstone is illuminated by a non-UV light source (e.g., a daylight approximating light source) and a fluorescence image for when the gemstone is illuminated by a UV light source (e.g., set at a predetermined intensity).

In preferred embodiments, the angular difference between consecutive color images remains constant throughout the collection of all images. Any configurations disclosed herein (e.g., concerning image view angles and image rotational angles) can be applied to the image collection process. For example, if the camera is set up to take 30 pictures per second and one full rotation of the sample platform takes 3 seconds, 90 images will be collected after a full rotation. In some embodiments, platform surface completes at least a full rotation with respect to the image capturing component. In some embodiments, the rotation is less than a full rotation. In some embodiments, the rotation is more than a full rotation; for example, 1.2 full rotations or less, 1.5 full rotations or less, 1.8 full rotations or less, 2 full rotations or less, 5 rotations, or 10 full rotations or less.

At step 9020, an outline mask is extracted for a non-UV illuminated image. Generally, an outline mask corresponds to the physical area occupied by a sample gemstone, represented by the full image of the sample gemstone. FIGS. 7A and 7B illustrate the differences for an image of the same diamond, before and after an outline mask is applied. As depicted in FIG. 7B, the outline mask highlights and clearly defines the edges of the diamond such that parameters like width and height can be more easily measured. The outline mask extraction process is done for all non-UV illuminated images taken for a given sample gemstone.

There are many methods for edge detection, and most of them can be grouped into two categories, search-based and zero-crossing based. The search-based methods detect edges by first computing a measure of edge strength, usually a first-order derivative expression such as the gradient magnitude, and then searching for local directional maxima of the gradient magnitude using a computed estimate of the local orientation of the edge, usually the gradient direction. The zero-crossing based methods search for zero crossings in a second-order derivative expression computed from the image in order to find edges, usually the zero-crossings of the Laplacian or the zero-crossings of a non-linear differential expression.

The edge detection methods known to date mainly differ in the types of smoothing filters that are applied and the way the measures of edge strength are computed. As many edge detection methods rely on the computation of image gradients, they also differ in the types of filters used for computing gradient estimates in the x- and y-directions.

Here, any applicable method for extracting an outline mask can be used, including for example an edge determining filter in commercially available software products such as Photoshop™ and etc. Additionally, for example, a simple algorithm can be developed in which any continuous areas in an image with a color value matching the background white color (as previously calibrated) is defined as black. As a result, a continuous black area will form the outline mask with an opening corresponding to the full image of a sample gemstone.

Based on outline masks, for each opening area corresponding to the full image of a sample gemstone, values of geometrical parameters (e.g., the width and height of the gemstone as illustrated in FIG. 7B) are determined. Outline masks are used for more accurate or automated measurements of the geometrical parameters. Essentially, the geometrical parameters are determined based on each outline mask, or more precisely, the opening of each outline mask. The measurements are taken for each image. After this step, a plurality set of measurement values are determined for the plurality of color images (or their corresponding outline masks), including, for example, a plurality if width measurements and a plurality of height measurements.

At step 9030, an apparent fluorescence area is extracted from an image captured under UV illumination for the same sample gemstone. The apparent fluorescence area is defined by the extent of fluorescence emission by portions of the sample gemstone that are capable of emitting fluorescence. As illustrated in FIGS. 7D and 7F, an apparent fluorescence area can be larger or smaller than the physical size of the gemstone. In particular, an apparent fluorescence area can be non-contiguous due to disconnected portions of the gemstones that emit fluorescence.

At steps 9040 through 9060, an apparent fluorescence area is overlaid on top of the corresponding outline mask in order to identifying a fluorescence mask. An important aspect of the overlaying step is to identify part of the apparent fluorescence area that falls outside of the physical boundaries of a sample gemstone (as defined by an outline mask). Because this part of the fluorescence emission does not correspond to any physical areas within the sample gemstone, including it in assessing fluorescence likely leads to errors. As such, in some embodiments, when there is any fluorescence outside of the physical boundaries of the sample gemstone, the corresponding fluorescence outside of the physical boundaries of the sample gemstone will be removed in step 9050. In contrast, in other embodiments, when there is no fluorescence outside of the physical boundaries of the sample gemstone, a fluorescence mask can be directly computed at step 9060, usually as the apparent fluorescence area itself.

For example, in FIG. 7D(a), fluorescence is present through the entire gemstone resulting in a large and contiguous apparent fluorescence area depicted in FIG. 7D(b). In this case, a fluorescence mask is a composite of the outline mask and the apparent fluorescence area, obtained by removing all areas beyond the physical boundaries of the sample gemstone (i.e., the outline mask). A fluorescence mask is identified by overlaying the apparent fluorescence area onto the outline mask and then removing any fluorescence beyond the physical boundaries of the outline mask. The fluorescence mask is the intersecting composition of the apparent fluorescence area and outline mask. In the particular example, because the apparent fluorescence area is contiguous and an outline mask is always contiguous, the resulting fluorescence mask is essentially the outline mask, as outlined in steps 9050 and 9060. The scenario illustrated in FIGS. 7E and 7F is a bit different. Here, fluorescence is emitted by disconnected parts of the sample gemstone, resulting in a non-contiguous apparent fluorescence area, as shown in FIG. 7F(b). Once again, a fluorescence mask is identified by overlaying the apparent fluorescence area onto the outline mask and then removing any fluorescence beyond the physical boundaries of the outline mask. In this particular example, there is no fluorescence outside of the physical boundaries of the sample gemstone (i.e., the outline mask). The resulting fluorescence mask corresponds to the apparent fluorescence area in FIG. 7F(b), as outlined in steps 9050 and 9060.

It will be understood that, if the extracted apparent fluorescence area is non-contiguous but also extends beyond the physical boundaries of the sample gemstone (i.e., the outline mask), the resulting fluorescence mask will be the apparent fluorescence area with the area outside the boundaries of the outline mask excluded (e.g., steps 9050 and 9060). Once again, the fluorescence mask is identified by overlaying the apparent fluorescence area; e.g., FIG. 7C(b), onto the outline mask for the gemstone; e.g., FIG. 7D(b).

Any area in the apparent fluorescence area that is outside of the boundaries defined by the outline mask will be eliminated. The remaining portion of the apparent fluorescence area intersecting with the outline mask corresponds to the fluorescence mask.

In some embodiments, the fluorescence mask corresponds to 20% or less of the entire gemstone, 25% or less of the entire gemstone, 30% or less of the entire gemstone, 35% or less of the entire gemstone, 40% or less of the entire gemstone, 45% or less of the entire gemstone, 50% or less of the entire gemstone, 55% or less of the entire gemstone, 60% or less of the entire gemstone, 65% or less of the entire gemstone, 70% or less of the entire gemstone, 75% or less of the entire gemstone, 80% or less of the entire gemstone, 85% or less of the entire gemstone, 90% or less of the entire gemstone, or 100% or less of the entire gemstone. In some embodiments, the fluorescence mask corresponds to the entire physical area of the sample gemstone.

Figure 9B:
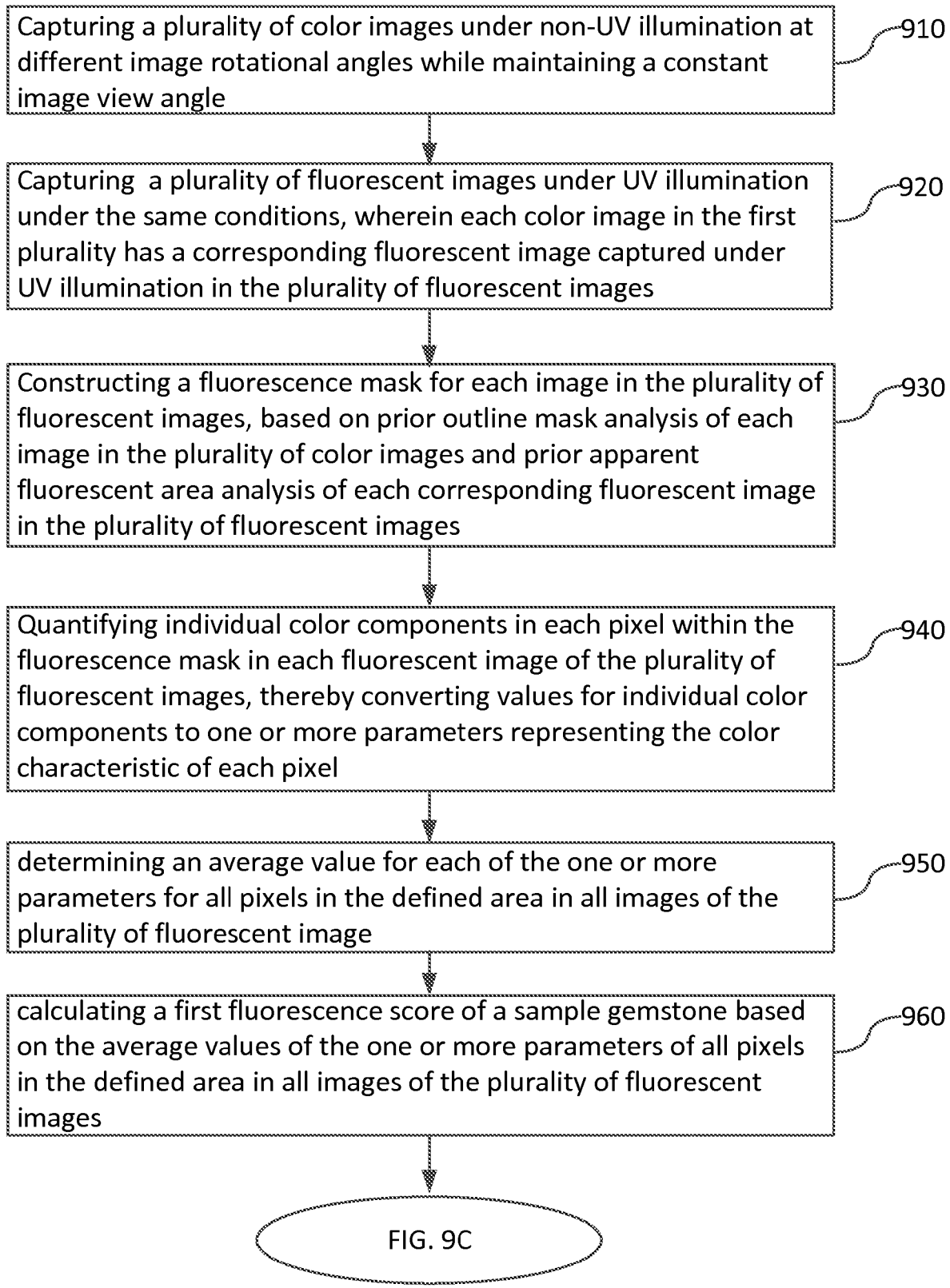
FIG. 9B depicts an exemplary process for a data collection and analysis.
Figure 9C:
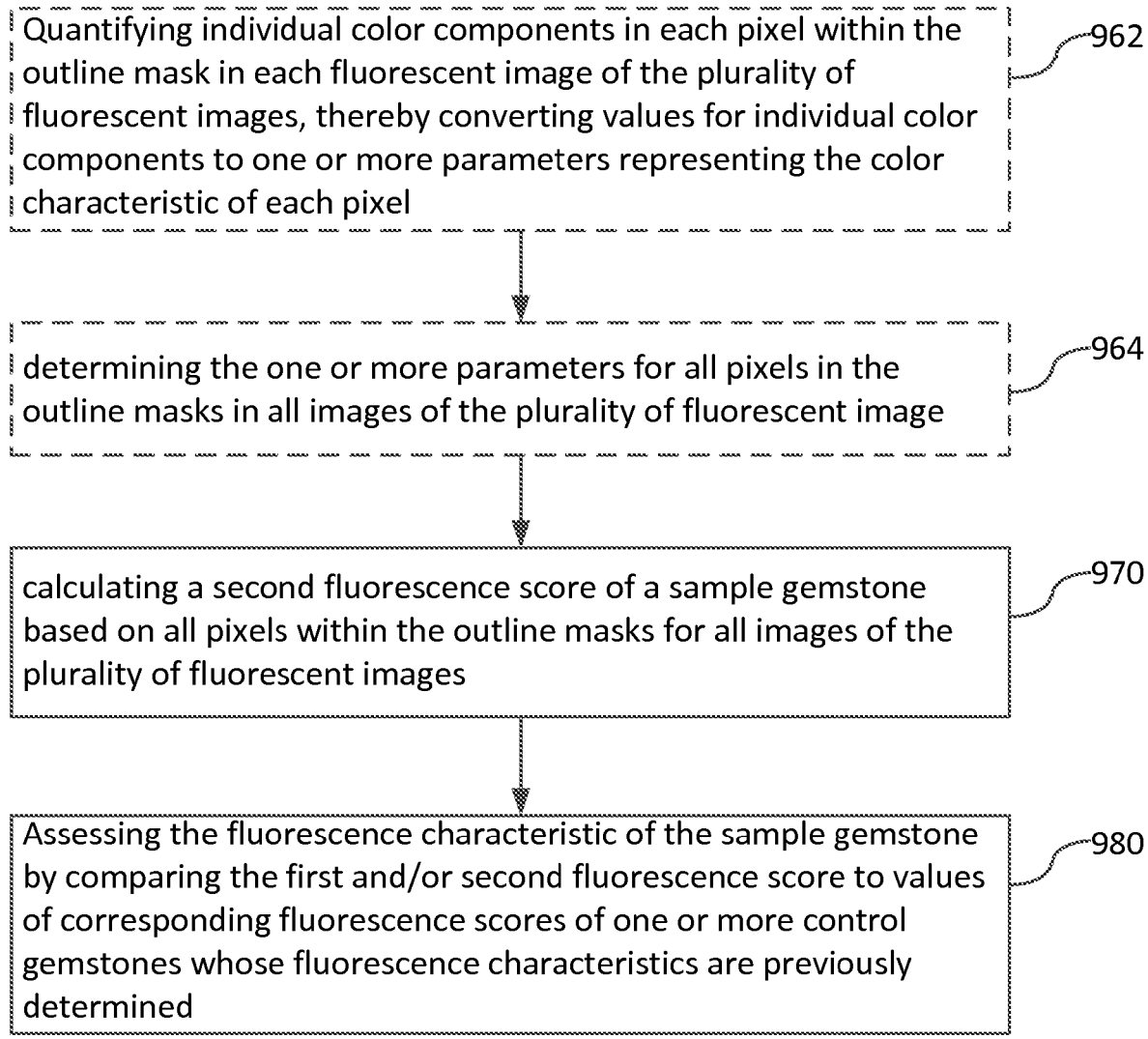
FIG. 9C depicts an exemplary process for a data collection and analysis.

For improved accuracy and consistency, only pixels within the fluorescence mask will be subject to computation and further analysis (e.g., step 900). An exemplary data collection, computation and analysis process is illustrated in FIGS. 9B and 9C.

At step 910, a plurality of images are captured of a sample gemstone under non-UV illumination. The color images are captured at different image rotational angles while the image view angle remains constant. Considerations that affect data collection are all applicable.

At step 920, a plurality of fluorescent images are captured of a sample gemstone under UV illumination. The color images are captured at different image rotational angles while the image view angle remains constant. Considerations that affect data collection are all applicable. The terms "fluorescent image" and "fluorescence image" will be used interchangeably.

At step 930, a fluorescence mask is applied to each fluorescence image in the plurality of fluorescent images. Exemplary methods for computing a fluorescence mask has been illustrated in FIG. 9A and described previously.

At step 940, pixels within the fluorescence mask are subject to quantitative analysis of the fluorescence images. For example, each pixel can be analyzed to quantify the values of all color components in the particular pixel. The number of color component is determined by the algorithm according to which the pixel is encoded when the color image is first captured. In some embodiments, the image is converted from its capturing color mode (e.g., CMYK) to a different color mode (e.g., RGB). After values are quantified for each color component in each pixel within the fluorescence mask, an average value can be calculated for each color component in a given fluorescence image. The process can be repeated for all images to calculate average value of each color component in all fluorescence images. Eventually, a final average value can be calculated for each color component based on information from all fluorescence images.

At step 950, the conversion process is carried out for all pixels within a defined area in an image in order to calculate average values of the one or more parameters. The steps of 910-950 can be repeated for all images in the plurality of color images. Eventually, average values of the one or more parameters (e.g., L*, a*, and b*) can be calculated for each color component based on information from all images.

At step 960, a first fluorescence score is calculated based on the values of the one or more parameters. For example, here the first fluorescence score can be chroma (C*) and hue (h) values, calculated based on CIE color space values (e.g., L*, a*, and b*); e.g., based on the following equations (FIG. 10):

$$C* = \sqrt{(a*)^2 + (b*)^2}$$
$$h = \tan^{-1}\left(\frac{b*}{a*}\right)$$

In some embodiments, color images are analyzed using the standards (e.g., tables of color matching functions and illuminants as a function of wavelength) published by CIE. A plot of the standard daylight illuminant with a correlated color temperature of 6500 K, $D_{65}$. This illuminant is represented here by the function $H_{D65}(\lambda)$. The color matching functions: $\bar{x}(\lambda)$, $\bar{y}(\lambda)$, $\bar{z}(\lambda)$ are used to calculate colorimetry parameters.

In some embodiments, the first fluorescence score represents the color or hue characteristics of the fluorescence emitted by the sample gemstone.

FIG. 9C continues to illustrate an exemplary process for fluorescence grade analysis. At step 962, individual color components in each pixel within the physical area of the gemstone in a fluorescent image (e.g., defined by the corresponding outline mask) are quantified. In some embodiments, each pixel is broken into three values representing the colors red (R), green (G) and blue (B). In some embodiments, each pixel is broken into three values representing the colors cyan (C), magenta (M), yellow (Y) and black (K). In some embodiments, the image is converted from its capturing color mode (e.g., CMYK) to a different color mode (e.g., RGB), or vice versa. The individual color components are then used to compute one or more parameters, for example, CIE color space values (e.g., L*, a*, and b*).

At step 964, the one or more parameters (e.g., L*, a*, and b*) are computed for all fluorescent images collected for a particular gemstone during one session (e.g., under the same illumination conditions while the image capture component (e.g., a camera) is configured under the same setting.

At step 970, a second fluorescence score is calculated for the same gemstone. In some embodiments, the second fluorescence score represents the fluorescence intensity of the gemstone. In some embodiments, the second fluorescence score represents the average fluorescence intensity of the gemstone according to the all the fluorescence images taken; for example, the average L* value.

At step 980, values of the first and/or second fluorescence scores, e.g., L*, C*, h* are compared to previously determined standard values of corresponding control gemstones to assign a fluorescence grade to the sample gemstone. The previously determined standard values are obtained for control gemstones using the same or a similar process. For example, one or more sets of sample stones, which share the same or similar color, proportion or shape characteristic and whose fluorescence grading values have been previously determined, are used as the control gemstones or grading standards. In some embodiments, the fluorescence color is evident. In some embodiments, the fluorescence color can be too weak for accurate identification. In such cases, the first and/or second fluorescence scores of the sample gemstone can be compared with multiple sets of control gemstones, each of a different color.

An example of computing color characteristics (e.g., L*, a* and b*) is as follows. As diamond is a transparent material, the sum of transmission spectrum T(λ) and reflection spectrum R(λ) is used in the calculation of the tristimulus values, X, Y and Z:

$$X = \Sigma_{\lambda=380}^{780} H_{D65}(\lambda)(T(\lambda)+R(\lambda))\bar{x}(\lambda)$$

$$Y = \Sigma_{\lambda=380}^{780} H_{D65}(\lambda)(T(\lambda)+R(\lambda))\bar{y}(\lambda)$$

$$Z = \Sigma_{\lambda=380}^{780} H_{D65}(\lambda)(T(\lambda)+R(\lambda))\bar{z}(\lambda).$$

The chromaticity coordinates, x and y, are then defined as:

$$x = \frac{X}{X+Y+Z}$$
$$y = \frac{Y}{X+Y+Z}$$

An attempt to achieve a "perceptually uniform" colour space is the CIE 1976 colour space, otherwise known as the CIELAB colour space. Its parameters are calculated from the tristimulus values as follows: lightness, $$L^* = 116(Y/Y_W)^{\frac{1}{3}} - 16$$

red-green parameter, $$a^* = 500\left[(X/X_W)^{\frac{1}{3}} - (Y/Y_W)^{\frac{1}{3}}\right]$$

and yellow-blue parameter, $$b^* = 200\left[(Y/Y_W)^{\frac{1}{3}} - (Z/Z_W)^{\frac{1}{3}}\right],$$

where Xw, Yw and Zw are the tristumulus values for the white point corresponding to the chosen illuminant, in this case D65.

$$X_w = \sum_{\lambda=380}^{780} H_{D65}(\lambda)\bar{x}(\lambda)$$

$$Y_w = \sum_{\lambda=380}^{780} H_{D65}(\lambda)\bar{y}(\lambda)$$

$$Z_w = \sum_{\lambda=380}^{780} H_{D65}(\lambda)\bar{z}(\lambda)$$

The saturation or chroma is expressed as:

$$C_{ab}^* = (a^{*2} + b^{*2})^{\frac{1}{3}}$$

and the hue angle is expressed as: $h_{ab} = \tan^{-1}(b^*/a^*)$.

Sources are available for image/color conversion and transformation. For example the Open CV project hosted at the docs<dot>opencv<dot>org can be used to convert RGB values to CIE L, a, b values. In addition, the same or similar resources allows conversion between RGB values and hue-saturation-value (HSV) values, between RGB values and hue-saturation-lightness (HSL) values, between RGB values and CIE Luv values in the Adams chromatic valence color space.

The present invention can be implemented as a computer system and/or a computer program product that comprises a computer program mechanism embedded in a computer readable storage medium. Further, any of the methods of the present invention can be implemented in one or more computers or computer systems. Further still, any of the methods of the present invention can be implemented in one or more computer program products. Some embodiments of the present invention provide a computer system or a computer program product that encodes or has instructions for performing any or all of the methods disclosed herein. Such methods/instructions can be stored on a CD-ROM, DVD, magnetic disk storage product, or any other computer readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise, by transmission of a computer data signal (in which the software modules are embedded) either digitally or on a carrier wave.

Some embodiments of the present invention provide a computer system or a computer program product that contains any or all of the program modules as disclosed herein. These program modules can be stored on a CD-ROM, DVD, magnetic disk storage product, or any other computer readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Fluorescence Grading for Regular Stones

Figure 10:
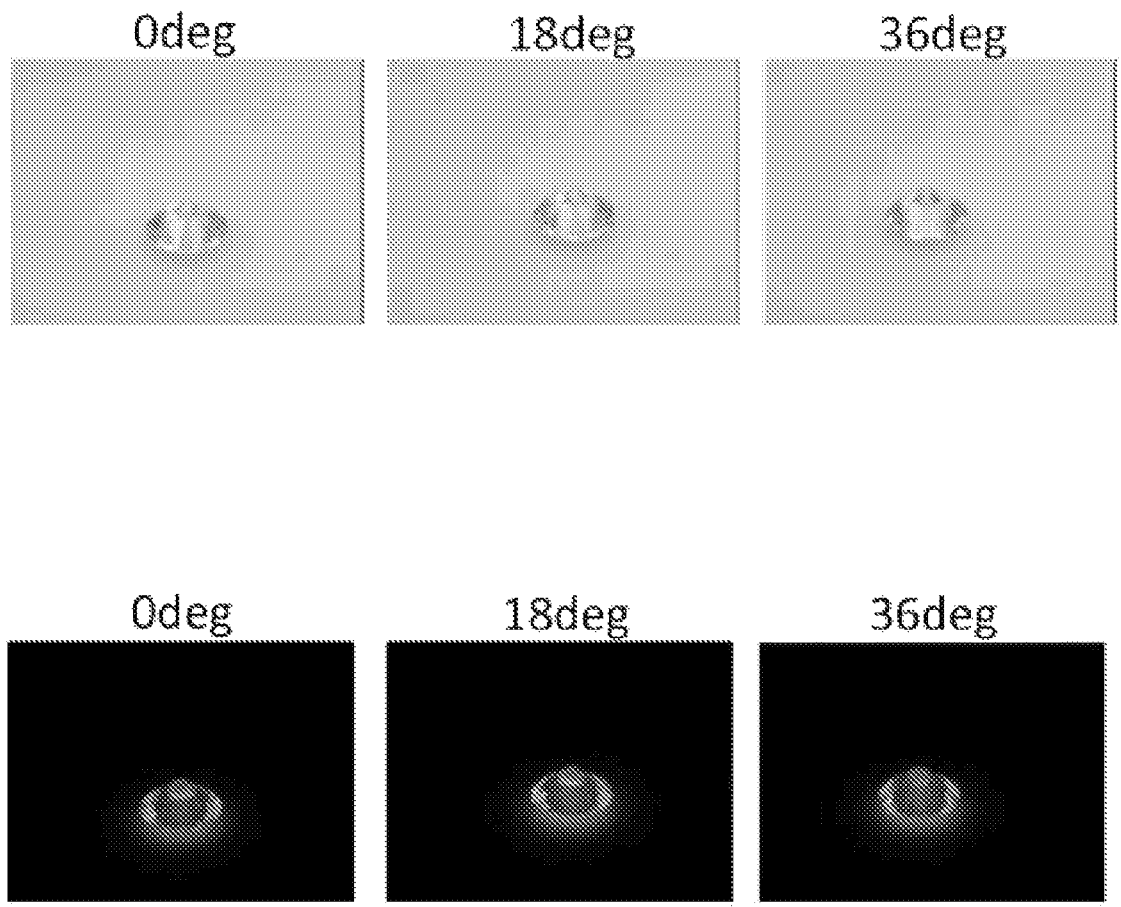
FIG. 10 depicts exemplary images taken under regular illumination and UV illumination.

FIG. 10 shows images of a sample gemstone taken under both daylight approximately light source (top 3 images) and under UV illumination (bottom 3 images). Under UV illumination, portions within the gemstone that emit fluorescence at different strength are evident.

Example 2

Validation of Fluorescence Emission Levels in Reference Stones

In this example, 4 reference stones with different strengths in fluorescence emission were subject to analysis. Image view angle was set at 32 degree. A Point Grey GS3-U3-28S5C camera was used to capture the images under regular and UV illuminations. Here, top UV illumination was provided by UV LEDs in combination with a band-pass filter and collimation lens.

FIG. 11 illustrates that, with the except of C values, both L and h values (in particular L values) correlate with the strengths of fluorescence emission observed in the reference stones.

Example 3

Gemstone with Inhomogeneous Fluorescence Distribution

Figure 12:
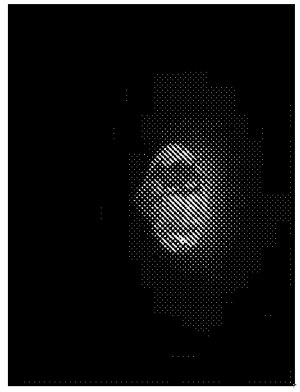
FIG. 12 depicts an exemplary embodiment, illustrating inhomogeneous fluorescence emission.
Figure 12:
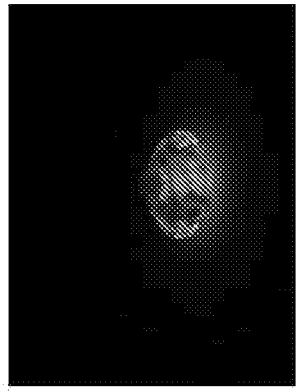
Figure 12:
Figure 12:
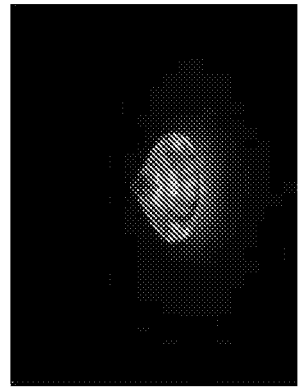

Images in FIG. 12 show a gemstone with inhomogeneous fluorescence distribution. At different image rotational angles (0 degree, 120 degree and 240 degree), different levels of fluorescence emission were observed. When each image was evaluated individually, the resulting L, C, H values suggested different machine grading of fluorescence strength. However, when L, C, H values were computed by averaging the effects from all images, machine grading score and visual inspection grading score became consistent.

Example 4

Fancy Shaped Stones with Blue Fluorescence

FIG. 13 depicts gemstones of fancy shapes but all with blue fluorescence. Here, image view angle was set at 32 degree. A Point Grey GS3-U3-28S5C camera was used to capture the images under regular and UV illuminations. Here, top UV illumination was provided.

The stones were of different shapes and sizes. After applying the analysis disclosed herein, the resulting machine fluorescence grading score for each stone was the same as the fluorescence grading score provided by human visual inspection. Here, the stones emitted blue fluorescence at different levels.

Example 5

Gemstones with Different Fluorescence Colors

FIG. 14 depicts two gemstones emitting different fluorescence color: the one on the left side emitted green fluorescence while the one on the right side emitted yellow fluorescence. Here, image view angle was set at 32 degree. A Point Grey GS3-U3-28S5C camera was used to capture the images under regular and UV illuminations. Here, top UV illumination was provided.

Again, after applying the analysis disclosed herein, the resulting machine fluorescence grading score for each stone was the same as the fluorescence grading score provided by human visual inspection. Here, the stones emitted different colors of fluorescence.

Example 6

Gemstones with Different Sizes and Fluorescence Colors

FIG. 15 depicts two gemstones emitting different fluorescence color: the one on the left side emitted yellow fluorescence while the one on the right side emitted orange fluorescence. Here, image view angle was set at 20 degree. A Point Grey GS3-U3-28S5C camera was used to capture the images under regular and UV illuminations. Here, top UV illumination was provided.

After applying the analysis disclosed herein, the resulting machine fluorescence grading score for each stone was the same as the fluorescence grading score provided by human visual inspection. Here, the two sample stones had drastically different sizes: one is almost three times as big as the other. In addition, the stones emitted different colors of fluorescence.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

I claim:

1. A method of assessing a fluorescence characteristic of a sample gemstone, the method comprising:
   by a computer with a processor and memory,
   receiving a digital pixelated first color image of the sample gemstone at a first image rotation angle and a first image view angle,
     wherein the first color image is taken under a daylight approximating non-UV light source;
   receiving a digital pixelated first fluorescence image of the sample gemstone at the first image rotation angle and the first image view angle,
     wherein the first fluorescence image is taken under a UV light source;
   receiving a digital pixelated second color image of the sample gemstone at a second image rotation angle and the first image view angle,
     wherein the second color image is taken under a daylight approximating non-UV light source;
   receiving a digital pixelated second fluorescence image of the sample gemstone at the second image rotation angle and the first image view angle,
     wherein the second fluorescence image is taken under a UV light source;
   determining, by the computer, an outline mask from the first color image and the second color image,
     wherein the outline mask excludes all background image outside of boundary lines of the sample gemstone in the images;
   based on the outline mask, determining values of geometrical parameters;
   determining an apparent fluorescence area of the sample gemstone, by the computer for the first fluorescence image and the second fluorescence image;
   generating a fluorescence mask by overlaying, by the computer, the determined apparent fluorescence area on the outline mask;
   determining, by the computer, if any part of the fluorescence area falls outside of the outline mask;
   removing, by the computer, any part of the fluorescence area falls outside of the outline mask;
   analyzing the remaining fluorescence area determined to be inside of the outline mask to assign a grade.

2. The method of claim 1 wherein the outline mask is determined using edge detection of the boundary lines of the sample gemstone.

3. The method of claim 2 wherein the edge detection is search-based by measuring an edge strength with a first-order derivative expression and searching for local directional maxima of gradient magnitude.

4. The method of claim 2 wherein the edge detection is zero-crossing based by searching for zero crossings in a second-order derivative expression computed from the first color image to find edges.

5. The method of claim 1 wherein the geometrical parameters include height and width.

6. The method of claim 1 wherein the analysis of the image inside the outline mask is an analysis of the pixels for quantitative analysis.

7. The method of claim 6 further comprising applying, by the computer, an algorithm to each pixel in the fluorescence image inside the outline mask to determine a color value for each corresponding pixel.

8. The method of claim 7 further comprising, converting the image pixels from CMYK to RGB values and using the RGB values to determine a color value for each corresponding pixel.

9. The method of claim 6 further comprising, determining, by the computer, converting the color values to parameters representing a color characteristic of each pixel.

10. The method of claim 9 further comprising, by the computer, calculating an average value for each parameter for all pixels inside the outline mask.

11. The method of claim 10 further comprising, by the computer, calculating a fluorescence score of the sample gemstone based on the average values of the parameters.

12. A non-transitory computer readable media with instructions for a method of assessing a fluorescence characteristic of a sample gemstone, the method comprising:
by a computer with a processor and memory,
receiving a digital pixelated first color image of the sample gemstone at a first image rotation angle and a first image view angle,
wherein the first color image is taken under a daylight approximating non-UV light source;
receiving a digital pixelated first fluorescence image of the sample gemstone at the first image rotation angle and the first image view angle,
wherein the first fluorescence image is taken under a UV light source;
receiving a digital pixelated second color image of the sample gemstone at a second image rotation angle and the first image view angle,
wherein the second color image is taken under a daylight approximating non-UV light source;
receiving a digital pixelated second fluorescence image of the sample gemstone at the second image rotation angle and the first image view angle,
wherein the second fluorescence image is taken under a UV light source;
determining, by the computer, an outline mask from the first color image and the second color image,
wherein the outline mask excludes all background image outside of boundary lines of the sample gemstone in the images;
based on the outline mask, determining values of geometrical parameters;
determining an apparent fluorescence area of the sample gemstone, by the computer for the first fluorescence image and the second fluorescence image;
generating a fluorescence mask by overlaying, by the computer, the determined apparent fluorescence area on the outline mask;
determining, by the computer, if any part of the fluorescence area falls outside of the outline mask;
removing, by the computer, any part of the fluorescence area falls outside of the outline mask;
analyzing the remaining fluorescence area determined to be inside of the outline mask to assign a grade.

13. The non-transitory computer readable media of claim 12 wherein the outline mask is determined using edge detection of the boundary lines of the sample gemstone.

14. The non-transitory computer readable media of claim 13 wherein the edge detection is search-based by measuring an edge strength with a first-order derivative expression and searching for local directional maxima of gradient magnitude.

15. The non-transitory computer readable media of claim 13 wherein the edge detection is zero-crossing based by searching for zero crossings in a second-order derivative expression computed from the first color image to find edges.

16. The non-transitory computer readable media of claim 12 wherein the geometrical parameters include height and width.

17. The non-transitory computer readable media of claim 12 wherein the analysis of the image inside the outline mask is an analysis of the pixels for quantitative analysis.

18. The non-transitory computer readable media of claim 17 further comprising applying, by the computer, an algorithm to each pixel in the fluorescence image inside the outline mask to determine a color value for each corresponding pixel.

19. The non-transitory computer readable media of claim 18 further comprising, converting the image pixels from CMYK to RGB values and using the RGB values to determine a color value for each corresponding pixel.

20. The non-transitory computer readable media of claim 17 further comprising, determining, by the computer, converting the color values to parameters representing a color characteristic of each pixel;
calculating an average value for each parameter for all pixels inside the outline mask; and
calculating a fluorescence score of the sample gemstone based on the average values of the parameters.

* * * * *